US006734287B1

(12) United States Patent
Lawton et al.

(10) Patent No.: US 6,734,287 B1
(45) Date of Patent: May 11, 2004

(54) SPECIFIC BINDING PROTEINS FOR TREATING CANINE ALLERGY

(75) Inventors: Robert Lawton, Gorham, ME (US); Brion Mermer, Cumberland, ME (US); Greg Francoeur, North Yarmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 09/281,760

(22) Filed: Mar. 30, 1999

Related U.S. Application Data

(63) Continuation-in-part of application No. 09/058,331, filed on Apr. 9, 1998, now abandoned.

(51) Int. Cl.[7] ................................................ C07K 16/00

(52) U.S. Cl. ................................ 530/387.9; 530/387.3; 530/388.1

(58) Field of Search ........................... 530/387.9, 387.3, 530/388.1, 387.1; 424/139.1

(56) References Cited

U.S. PATENT DOCUMENTS

| | | | | |
|---|---|---|---|---|
| 4,940,782 | A | | 7/1990 | Rup et al. |
| 5,321,123 | A | * | 6/1994 | Griffin et al. |
| 5,342,924 | A | | 8/1994 | Chang |
| 5,422,258 | A | | 6/1995 | Chang |
| 5,428,133 | A | * | 6/1995 | Chang |
| 5,541,776 | A | * | 7/1996 | Kobayashi et al. |
| 5,543,144 | A | | 8/1996 | Chang |
| 5,629,415 | A | * | 5/1997 | Hollis et al. |
| 5,653,980 | A | | 8/1997 | Hellman |
| 5,670,626 | A | * | 9/1997 | Chang |

FOREIGN PATENT DOCUMENTS

| | | | |
|---|---|---|---|
| JP | 08151396 | | 6/1996 |
| WO | WO 89/06138 | | 7/1989 |
| WO | WO 92/09628 | | 6/1992 |
| WO | WO 93/08282 | | 4/1993 |
| WO | WO 94/20127 | | 9/1994 |
| WO | WO 94/20533 | | 9/1994 |
| WO | WO 95/11255 | | 4/1995 |
| WO | WO 95/31728 | * | 11/1995 |
| WO | WO 97/21820 | | 6/1997 |

OTHER PUBLICATIONS

Hill et al. Vet Immunol. & Immunother. 44:105–113, 1995.*

Liderman et al. Mol. Immunol 28:471–1181, 1991.*

Aloza et al. J. Prot. Chem. 11:433–444, 1992.*

Ngo et al.; in The Protein Folding Problem and Tertiary Structure Prediction, 1994, Merz et al., (ed.), Birkhauser, MA, pp. 433 and 492–495.*

Coleman et al. (Research in Immunology, 1994; 145(1): 33–36.*

Bascom, Roger A., *Cloning of the human and murine ROM1 genes:genomic organization and sequence conservation*, Human Molecular Genetics, vol. 2, No. 4, pp. 385–391, 1993.

Burt, D. S. et al., *Analysis of the Interaction Between Rat Immunoglobulin E and Rat Mast Cells using Anti–Peptide Antibodies; Molecular Immunology*, vol. 24, No. 4, pp 379–389; XP000917287, 1987.

(List continued on next page.)

*Primary Examiner*—Patrick J. Nolan

(74) *Attorney, Agent, or Firm*—McDonnell Boehnen Hulbert & Berghoff

(57) ABSTRACT

Disclosed are binding proteins that specifically bind to an isolated and purified peptide comprising a leucine positioned two peptide bonds away from a tyrosine-arginine pair. Other binding proteins of the invention include those that specifically bind to an isolated and purified peptide with the sequence cysteine-blank-blank-proline-histidine-blank-blank-blank-cysteine (SEQ ID NO:6) or cysteine-blank-proline-histidine-blank-proline-blank-blank-cysteine (SEQ ID NO:9).

8 Claims, 14 Drawing Sheets

OTHER PUBLICATIONS

Presta, L.G. et al., *Humanization of an Antibody Directed Against IgE; The Journal of Immunology*; vol. 151, pp 2623–26321; XP002094432, 1993.

Bascom, Roger A. et al., *Cloning of the Human and Murine ROM1 genes; Genomic Organization and Sequence Conservation; Human Molecular Genetics*; 1993; vol 2, No. 4, PP 385–391; XP000915640; 1993.

D. Deboer et al., *Production and Characterization of Mouse Monoclonal Antibodies Directed Against Canine IgE and IgG*, Veterinary Immunology and Immunopathology, vol. 37, 1993, pp. 183–199 XP000647974, figure 2, table 3.

Konieczny, A., et al., *The Major Dog Allergens, Can f1 and Can f2, are Silvary Lipocalin Proteins: Cloning and Immunological Characterization of the Recombinant Forms*, Immunology, Vol 92, 1997, pp. 577–586, XP000915647.

Aurialt, C., Wolowczuk, I., Gras–Masse, H., et al., Peptide Res., 4: 6–11 (1991).

DeBoer, et al., Veterinary Immunology and Immunopathology, 37: 183–199 (1993).

Hill and DeBoer, Am. J. Vet. Res., 55(7): 944–948 (Jul. 1994).

Ishida, et al., EMBO Journal, 1: 1117–1123 (1982).

Patel, et al, Immunogenetics, 41:282–286 (Mar. 22, 1995).

Posnett, D. N., McGrath, H., and Tam, J. P., J. Biol. Chem., 263: 1719–1725 (1988).

Tam, Proc. Natl. Acad. Sci. U. S. A, 85: 5409–5413 (1988).

Tam, J. P., and Zavala, F., J. Immunol. Meth., 124: 53–61 (1989).

* cited by examiner

| LIBRARY | SEQUENCE OF DISPLAYED PEPTIDE | ISOLATE |
|---|---|---|
| PhDc7c | C S N P H V T H C | M13 1&9 |
| PhDc7c | C S H P H L T H C | M13 7 |
| PhDc7c | C S N P H I T Q C | M13 10 |
| PhDc7c | C M N P H I T H C | M13 14 |
| PhDc7c | C T N P H N P Y C | M13 2&8 |
| PhDc7c | C P N P H N P Y C | M13 3&5 |
| PhD12 | V T L C P N P H I P M C | M13 48 |
| PhDc7c | C H P H L P K S C | M13 4&12 |
| PhDc7c | C H P H L P K R C | M13 6 |
| | Y C R V T H P H L P K D I V R S I | Canine IgE |

FIG.6

IgE ALIGNMENT 15A.2 EPITOPE

| | SPECIES |
|---|---|
| Y C R V T H P H L P K D I V R S I | Canine |
| Q C R V T H P H L P R A L M R S T | Human |
| Q C R V T H P H L P R A L V R S T | Green Monkey |
| Q C K V T H P D L P L V I V R S I | Cat |
| Y C N V T H P D L P K P I L R S I | Swine |
| Q C I V D H P D F P * * I V R S I | Mouse |
| K C T V S H P D L P R E * W R S I | Horse |

*Denotes a deletion

FIG.7

SEQUENCE LISTING

```
<160> NUMBER OF SEQ ID NOS: 39

<210> SEQ ID NO 1
<211> LENGTH: 5
<212> TYPE: PRT
<213> ORGANISM: Canis familiaris
<220> FEATURE:
<221> NAME/KEY: PEPTIDE
<222> LOCATION: (2)...(3)
<223> OTHER INFORMATION: Xaa = any amino acid

<400> SEQUENCE: 1

Leu Xaa Xaa Tyr Arg
 1               5


<210> SEQ ID NO 2
<211> LENGTH: 5
<212> TYPE: PRT
<213> ORGANISM: Canis familiaris
<220> FEATURE:
<221> NAME/KEY: PEPTIDE
<222> LOCATION: (3)...(4)
<223> OTHER INFORMATION: Xaa = Any amino acid

<400> SEQUENCE: 2

Tyr Arg Xaa Xaa Leu
 1               5


<210> SEQ ID NO 3
<211> LENGTH: 8
<212> TYPE: PRT
<213> ORGANISM: Canis familiaris
<220> FEATURE:
<221> NAME/KEY: PEPTIDE
<222> LOCATION: (2)...(3)
<223> OTHER INFORMATION: Xaa = Any amino acid
<220> FEATURE:
```

-continued

```
<221> NAME/KEY: PEPTIDE
<222> LOCATION: (6)...(7)
<223> OTHER INFORMATION: Xaa = Any amino acid

<400> SEQUENCE: 3

Leu Xaa Xaa Tyr Arg Xaa Xaa Leu
 1               5


<210> SEQ ID NO 4
<211> LENGTH: 7
<212> TYPE: PRT
<213> ORGANISM: Canis familiaris

<400> SEQUENCE: 4

       Thr Leu Leu Glu Tyr Arg Met
        1               5


<210> SEQ ID NO 5
<211> LENGTH: 11
<212> TYPE: PRT
<213> ORGANISM: Canis familiaris

<400> SEQUENCE: 5

Gly Met Asn Leu Thr Trp Tyr Arg Glu Ser Lys
 1               5                   10


<210> SEQ ID NO 6
<211> LENGTH: 9
<212> TYPE: PRT
<213> ORGANISM: Canis familiaris
<220> FEATURE:
<221> NAME/KEY: PEPTIDE
<222> LOCATION: (2)...(3)
<223> OTHER INFORMATION: Xaa = Any amino acid
<220> FEATURE:
<221> NAME/KEY: PEPTIDE
<222> LOCATION: (6)...(8)
<223> OTHER INFORMATION: Xaa = Any amino acid

<400> SEQUENCE: 6

Cys Xaa Xaa Pro His Xaa Xaa Xaa Cys
 1               5


<210> SEQ ID NO 7
<211> LENGTH: 16
<212> TYPE: PRT
<213> ORGANISM: Canis familiaris

<400> SEQUENCE: 7

Ser Val Thr Leu Cys Pro Asn Pro His Ile Pro Met Cys Gly Gly Gly
 1               5                   10                  15


<210> SEQ ID NO 8
<211> LENGTH: 14
<212> TYPE: PRT
<213> ORGANISM: Canis familiaris

<400> SEQUENCE: 8

Ser Ala Cys Pro Asn Pro His Asn Pro Tyr Cys Gly Gly Gly
 1               5                   10


<210> SEQ ID NO 9
<211> LENGTH: 9
<212> TYPE: PRT
<213> ORGANISM: Canis familiaris
<220> FEATURE:
<221> NAME/KEY: PEPTIDE
```

-continued

<222> LOCATION: (2)...(2)
<223> OTHER INFORMATION: Xaa = Any amino acid
<220> FEATURE:
<221> NAME/KEY: PEPTIDE
<222> LOCATION: (5)...(5)
<223> OTHER INFORMATION: Xaa = Any amino acid
<220> FEATURE:
<221> NAME/KEY: PEPTIDE
<222> LOCATION: (7)...(8)
<223> OTHER INFORMATION: Xaa = Any amino acid

<400> SEQUENCE: 9

Cys Xaa Pro His Xaa Pro Xaa Xaa Cys
1 5

<210> SEQ ID NO 10
<211> LENGTH: 14
<212> TYPE: PRT
<213> ORGANISM: Canis familiaris

<400> SEQUENCE: 10

Ser Ala Cys His Pro His Leu Pro Lys Ser Cys Gly Gly Gly
1 5 10

<210> SEQ ID NO 11
<211> LENGTH: 12
<212> TYPE: PRT
<213> ORGANISM: Canis familiaris

<400> SEQUENCE: 11

Val Thr Leu Cys Pro Asn Pro His Ile Pro Met Cys
1 5 10

<210> SEQ ID NO 12
<211> LENGTH: 17
<212> TYPE: PRT
<213> ORGANISM: Canis familiaris

<400> SEQUENCE: 12

Ser Val Thr Leu Cys Pro Asn Pro His Ile Pro Met Cys Gly Gly Gly
1 5 10 15

Lys

<210> SEQ ID NO 13
<211> LENGTH: 7
<212> TYPE: PRT
<213> ORGANISM: Homo sapiens

<400> SEQUENCE: 13

Val Asn Leu Thr Trp Ser Arg
1 5

<210> SEQ ID NO 14
<211> LENGTH: 11
<212> TYPE: PRT
<213> ORGANISM: Felis catus

<400> SEQUENCE: 14

Gly Met Thr Leu Thr Trp Ser Arg Glu Asn Gly
1 5 10

<210> SEQ ID NO 15
<211> LENGTH: 11
<212> TYPE: PRT
<213> ORGANISM: Canis familiaris -continued

<400> SEQUENCE: 15

Gly Met Asn Leu Thr Trp Ser Arg Glu Ser Lys
1 5 10

<210> SEQ ID NO 16
<211> LENGTH: 9
<212> TYPE: PRT
<213> ORGANISM: Canis familiaris

<400> SEQUENCE: 16

Cys Pro Asn Pro His Ile Pro Met Cys
1 5

<210> SEQ ID NO 17
<211> LENGTH: 9
<212> TYPE: PRT
<213> ORGANISM: Canis familiaris

<400> SEQUENCE: 17

Cys Pro Asn Pro His Asn Pro Tyr Cys
1 5

<210> SEQ ID NO 18
<211> LENGTH: 9
<212> TYPE: PRT
<213> ORGANISM: Canis familiaris

<400> SEQUENCE: 18

Cys His Pro His Leu Pro Lys Ser Cys
1 5

<210> SEQ ID NO 19
<211> LENGTH: 9
<212> TYPE: PRT
<213> ORGANISM: Canis familiaris

<400> SEQUENCE: 19

Cys Ser Asn Pro His Val Thr His Cys
1 5

<210> SEQ ID NO 20
<211> LENGTH: 9
<212> TYPE: PRT
<213> ORGANISM: Canis familiaris

<400> SEQUENCE: 20

Cys Ser His Pro His Leu Thr His Cys
1 5

<210> SEQ ID NO 21
<211> LENGTH: 9
<212> TYPE: PRT
<213> ORGANISM: Canis familiaris

<400> SEQUENCE: 21

Cys Ser Asn Pro His Ile Thr Gln Cys
1 5

<210> SEQ ID NO 22
<211> LENGTH: 9
<212> TYPE: PRT
<213> ORGANISM: Canis familiaris

<400> SEQUENCE: 22

-continued

```
Cys Met Asn Pro His Ile Thr His Cys
 1               5


<210> SEQ ID NO 23
<211> LENGTH: 9
<212> TYPE: PRT
<213> ORGANISM: Canis familiaris

<400> SEQUENCE: 23

Cys Thr Asn Pro His Asn Pro Tyr Cys
 1               5


<210> SEQ ID NO 24
<211> LENGTH: 9
<212> TYPE: PRT
<213> ORGANISM: Canis familiaris

<400> SEQUENCE: 24

Cys Pro Asn Pro His Asn Pro Tyr Cys
 1               5


<210> SEQ ID NO 25
<211> LENGTH: 9
<212> TYPE: PRT
<213> ORGANISM: Canis familiaris

<400> SEQUENCE: 25

Cys His Pro His Leu Pro Lys Arg Cys
 1               5


<210> SEQ ID NO 26
<211> LENGTH: 17
<212> TYPE: PRT
<213> ORGANISM: Canis familiaris

<400> SEQUENCE: 26

Tyr Cys Arg Val Thr His Pro His Leu Pro Lys Asp Ile Val Arg Ser
 1               5                   10                  15

Ile


<210> SEQ ID NO 27
<211> LENGTH: 17
<212> TYPE: PRT
<213> ORGANISM: Homo sapiens

<400> SEQUENCE: 27

Gln Cys Arg Val Thr His Pro His Leu Pro Arg Ala Leu Met Arg Ser
 1               5                   10                  15

Thr


<210> SEQ ID NO 28
<211> LENGTH: 17
<212> TYPE: PRT
<213> ORGANISM: Cercopithecus aethiops

<400> SEQUENCE: 28

Gln Cys Arg Val Thr His Pro His Leu Pro Arg Ala Leu Val Arg Ser
 1               5                   10                  15

Thr


<210> SEQ ID NO 29
<211> LENGTH: 17
<212> TYPE: PRT
```

-continued

<213> ORGANISM: Felis catus

<400> SEQUENCE: 29

```
Gln Cys Lys Val Thr His Pro Asp Leu Pro Leu Val Ile Val Arg Ser
 1               5                  10                  15

Ile


<210> SEQ ID NO 30
<211> LENGTH: 17
<212> TYPE: PRT
<213> ORGANISM: Sus scrofa

<400> SEQUENCE: 30

Tyr Cys Asn Val Thr His Pro Asp Leu Pro Lys Pro Ile Leu Arg Ser
 1               5                  10                  15

Ile


<210> SEQ ID NO 31
<211> LENGTH: 15
<212> TYPE: PRT
<213> ORGANISM: Mus musculus

<400> SEQUENCE: 31

Gln Cys Ile Val Asp His Pro Asp Phe Pro Ile Val Arg Ser Ile
 1               5                  10                  15


<210> SEQ ID NO 32
<211> LENGTH: 16
<212> TYPE: PRT
<213> ORGANISM: Equus caballus

<400> SEQUENCE: 32

Lys Cys Thr Val Ser His Pro Asp Leu Pro Arg Glu Trp Arg Ser Ile
 1               5                  10                  15


<210> SEQ ID NO 33
<211> LENGTH: 1842
<212> TYPE: DNA
<213> ORGANISM: Canis familiaris
<220> FEATURE:
<221> NAME/KEY: misc_feature
<222> LOCATION: (136)..(136)
<223> OTHER INFORMATION: "n" stands for any nucleic acid
<220> FEATURE:
<221> NAME/KEY: misc_feature
<222> LOCATION: (413)..(414)
<223> OTHER INFORMATION: "n" stands for any nucleic acid
<220> FEATURE:
<221> NAME/KEY: misc_feature
<222> LOCATION: (451)..(451)
<223> OTHER INFORMATION: "n" stands for any nucleic acid
<220> FEATURE:
<221> NAME/KEY: misc_feature
<222> LOCATION: (460)..(462)
<223> OTHER INFORMATION: "n" stands for any nucleic acid
<220> FEATURE:
<221> NAME/KEY: misc_feature
<222> LOCATION: (500)..(500)
<223> OTHER INFORMATION: "n" stands for any nucleic acid
<220> FEATURE:
<221> NAME/KEY: misc_feature
<222> LOCATION: (530)..(530)
<223> OTHER INFORMATION: "n" stands for any nucleic acid
<220> FEATURE:
<221> NAME/KEY: misc_feature
<222> LOCATION: (568)..(568)
<223> OTHER INFORMATION: "n" stands for any nucleic acid
<220> FEATURE:
<221> NAME/KEY: misc_feature
```

-continued

```
<222> LOCATION: (847)..(849)
<223> OTHER INFORMATION: "n" stands for any nucleic acid
<220> FEATURE:
<221> NAME/KEY: misc_feature
<222> LOCATION: (853)..(853)
<223> OTHER INFORMATION: "n" stands for any nucleic acid
<220> FEATURE:
<221> NAME/KEY: misc_feature
<222> LOCATION: (1382)..(1382)
<223> OTHER INFORMATION: "n" stands for any nucleic acid
<220> FEATURE:
<221> NAME/KEY: misc_feature
<222> LOCATION: (1832)..(1832)
<223> OTHER INFORMATION: "n" stands for any nucleic acid
<220> FEATURE:
<221> NAME/KEY: CDS
<222> LOCATION: (167)..(448)
<223> OTHER INFORMATION:
<220> FEATURE:
<221> NAME/KEY: CDS
<222> LOCATION: (608)..(931)
<223> OTHER INFORMATION:
<220> FEATURE:
<221> NAME/KEY: CDS
<222> LOCATION: (1024)..(1344)
<223> OTHER INFORMATION:
<220> FEATURE:
<221> NAME/KEY: CDS
<222> LOCATION: (1419)..(1742)
<223> OTHER INFORMATION:

<400> SEQUENCE: 33

gtccagtgac ctccatctct gcccccatgc ttttccttct cagacgcccc ctggggccag      60

gagcaggata ccccaggtca acagcgggcc tggcatatga tggggtgaca gtcccaaggc     120

aggcactgac actggncctg tccccacagc caccagccag gacctg tct gtg ttc        175
                                                   Ser Val Phe
                                                   1

ccc ttg gcc tcc tgc tgt aaa gac aac atc gcc agt acc tct gtt aca       223
Pro Leu Ala Ser Cys Cys Lys Asp Asn Ile Ala Ser Thr Ser Val Thr
    5                   10                  15

ctg ggc tgt ctg gtc acc ggc tat ctc ccc atg tcg aca act gtg acc       271
Leu Gly Cys Leu Val Thr Gly Tyr Leu Pro Met Ser Thr Thr Val Thr
20                  25                  30                  35

tgg gac acg ggg tct cta aat aag aat gtc acg acc ttc ccc acc acc       319
Trp Asp Thr Gly Ser Leu Asn Lys Asn Val Thr Thr Phe Pro Thr Thr
                40                  45                  50

ttc cac gag acc tac ggc ctc cac agc atc gtc agc cag gtg acc gcc       367
Phe His Glu Thr Tyr Gly Leu His Ser Ile Val Ser Gln Val Thr Ala
            55                  60                  65

tcg ggc gag tgg gcc aaa cag agg ttc acc tgc agc gtg gct cac nnt       415
Ser Gly Glu Trp Ala Lys Gln Arg Phe Thr Cys Ser Val Ala His Xaa
        70                  75                  80

gag tcc acc gcc atc aac aag acc ttc agt gct aanccagggt tnnntggcca     468
Glu Ser Thr Ala Ile Asn Lys Thr Phe Ser Ala
    85                  90

catgacactg gagggagaag ggacaggctg gngaatgcgc catggctggt aacgcccagc     528

anatgtgggg ctggggctga cacatgagtc ccgtgggctn agagacacca ctgccacatg     588

gctgcctcta cttctagca tgt gcc tta aac ttc att ccg cct acc gtg aag      640
                     Cys Ala Leu Asn Phe Ile Pro Pro Thr Val Lys
                     95                  100                 105

ctc ttc cac tcc tcc tgc aac ccc gtc ggt gat acc cac acc acc atc       688
Leu Phe His Ser Ser Cys Asn Pro Val Gly Asp Thr His Thr Thr Ile
                110                 115                 120

cag ctc ctg tgc ctc atc tct ggc tac gtc cca ggt gac atg gag gtc       736
Gln Leu Leu Cys Leu Ile Ser Gly Tyr Val Pro Gly Asp Met Glu Val
```

-continued

```
            125                 130                 135

atc tgg ctg gtg gat ggg caa aag gct aca aac ata ttc cca tac act      784
Ile Trp Leu Val Asp Gly Gln Lys Ala Thr Asn Ile Phe Pro Tyr Thr
        140                 145                 150

gca ccc ggc aca aag gag ggc aac gtg acc tct acc cac agc gag ctc      832
Ala Pro Gly Thr Lys Glu Gly Asn Val Thr Ser Thr His Ser Glu Leu
    155                 160                 165

aac atc acc cag ggn nng tgn gta tcc caa aaa acc tac acc tgc cag      880
Asn Ile Thr Gln Gly Xaa Xaa Val Ser Gln Lys Thr Tyr Thr Cys Gln
170                 175                 180                 185

gtc acc tat caa ggc ttt acc ttt aaa gat gag gct cgc aag tgc tca      928
Val Thr Tyr Gln Gly Phe Thr Phe Lys Asp Glu Ala Arg Lys Cys Ser
                190                 195                 200

gag atggcccccc tgtcccccag aaacccagat gcgcgaggct cagagatgag           981
Glu

ggccaaggca cgccctcatg cagcctctca cacactgcag ag tcc gac ccc cga      1035
                                               Ser Asp Pro Arg
                                                       205

ggc gtg agc agc tac ctg agc cca ccc agc ccc ctt gac ctg tat gtc     1083
Gly Val Ser Ser Tyr Leu Ser Pro Pro Ser Pro Leu Asp Leu Tyr Val
            210                 215                 220

cac aag gcg ccc aag atc acc tgc ctg gta gtg gac ctg gcc acc atg     1131
His Lys Ala Pro Lys Ile Thr Cys Leu Val Val Asp Leu Ala Thr Met
        225                 230                 235

gaa ggc atg aac ctg acc tgg tac cgg gag agc aaa gaa ccc gtg aac     1179
Glu Gly Met Asn Leu Thr Trp Tyr Arg Glu Ser Lys Glu Pro Val Asn
    240                 245                 250

ccg gtc cct ttg aac aag aag gat cac ttc aat ggg acg atc aca gtc     1227
Pro Val Pro Leu Asn Lys Lys Asp His Phe Asn Gly Thr Ile Thr Val
255                 260                 265                 270

acg tct acc ctg cca gtg aac acc aat gac tgg atc gag ggc gag acc     1275
Thr Ser Thr Leu Pro Val Asn Thr Asn Asp Trp Ile Glu Gly Glu Thr
                275                 280                 285

tac tat tgc agg gtg acc cac ccg cac ctg ccc aag gac atc gtg cgc     1323
Tyr Tyr Cys Arg Val Thr His Pro His Leu Pro Lys Asp Ile Val Arg
            290                 295                 300

tcc att gcc aag gcc cct ggt gagccacggg cccaggggag gtgggcgggc        1374
Ser Ile Ala Lys Ala Pro Gly
        305

ctcctgancc ggagcctggg ctgaccccac acctatccac aggc aag cgt gcc ccc    1430
                                                 Lys Arg Ala Pro
                                                 310

ccg gat gtg tac ttg ttc ctg cca ccg gag gag gag cag ggg acc aag     1478
Pro Asp Val Tyr Leu Phe Leu Pro Pro Glu Glu Glu Gln Gly Thr Lys
    315                 320                 325

gac aga gtc acc ctc acg tgc ctg atc cag aac ttc ttc ccc gag gac     1526
Asp Arg Val Thr Leu Thr Cys Leu Ile Gln Asn Phe Phe Pro Glu Asp
330                 335                 340                 345

att tca gtg caa tgg ctg cga aac gac agc ccc atc cag aca gac cag     1574
Ile Ser Val Gln Trp Leu Arg Asn Asp Ser Pro Ile Gln Thr Asp Gln
                350                 355                 360

tac acc acc acg ggg ccc cac aag gtc tcg ggc tcc agg cct gcc ttc     1622
Tyr Thr Thr Thr Gly Pro His Lys Val Ser Gly Ser Arg Pro Ala Phe
            365                 370                 375

ttc atc ttc agt cgc ctg gtg gac tgg gag cag aaa aac aaa ttc acc     1670
Phe Ile Phe Ser Arg Leu Val Asp Trp Glu Gln Lys Asn Lys Phe Thr
        380                 385                 390

tgc caa gtg gtg cat gag gcg ctg tcc ggc tct agg atc ctc cag aaa     1718
Cys Gln Val Val His Glu Ala Leu Ser Gly Ser Arg Ile Leu Gln Lys
```

-continued

```
    395                 400                 405

tgg gtg tcc aaa acc ccc ggt aaa tgatgcccac cctcctcccg ccgccacccc    1772
Trp Val Ser Lys Thr Pro Gly Lys
410                 415

ccagggctcc acctgctggg gcaggggagg ggggctggca agaccctcca tctatccttn   1832

tcaataaaca                                                          1842


<210> SEQ ID NO 34
<211> LENGTH: 94
<212> TYPE: PRT
<213> ORGANISM: Canis familiaris
<220> FEATURE:
<221> NAME/KEY: misc_feature
<222> LOCATION: (83)..(83)
<223> OTHER INFORMATION: The 'Xaa' at location 83 stands for Asn, Ser,
      Thr, Ile, Asp, Gly, Ala, Val, His, Arg, Pro, Leu, Tyr, Cys, or
      Phe.
<220> FEATURE:
<221> NAME/KEY: misc_feature
<222> LOCATION: (136)..(136)
<223> OTHER INFORMATION: "n" stands for any nucleic acid
<220> FEATURE:
<221> NAME/KEY: misc_feature
<222> LOCATION: (413)..(414)
<223> OTHER INFORMATION: "n" stands for any nucleic acid
<220> FEATURE:
<221> NAME/KEY: misc_feature
<222> LOCATION: (451)..(451)
<223> OTHER INFORMATION: "n" stands for any nucleic acid
<220> FEATURE:
<221> NAME/KEY: misc_feature
<222> LOCATION: (460)..(462)
<223> OTHER INFORMATION: "n" stands for any nucleic acid
<220> FEATURE:
<221> NAME/KEY: misc_feature
<222> LOCATION: (500)..(500)
<223> OTHER INFORMATION: "n" stands for any nucleic acid
<220> FEATURE:
<221> NAME/KEY: misc_feature
<222> LOCATION: (530)..(530)
<223> OTHER INFORMATION: "n" stands for any nucleic acid
<220> FEATURE:
<221> NAME/KEY: misc_feature
<222> LOCATION: (568)..(568)
<223> OTHER INFORMATION: "n" stands for any nucleic acid
<220> FEATURE:
<221> NAME/KEY: misc_feature
<222> LOCATION: (847)..(849)
<223> OTHER INFORMATION: "n" stands for any nucleic acid
<220> FEATURE:
<221> NAME/KEY: misc_feature
<222> LOCATION: (853)..(853)
<223> OTHER INFORMATION: "n" stands for any nucleic acid
<220> FEATURE:
<221> NAME/KEY: misc_feature
<222> LOCATION: (1382)..(1382)
<223> OTHER INFORMATION: "n" stands for any nucleic acid
<220> FEATURE:
<221> NAME/KEY: misc_feature
<222> LOCATION: (1832)..(1832)
<223> OTHER INFORMATION: "n" stands for any nucleic acid

<400> SEQUENCE: 34

Ser Val Phe Pro Leu Ala Ser Cys Cys Lys Asp Asn Ile Ala Ser Thr
1               5                   10                  15

Ser Val Thr Leu Gly Cys Leu Val Thr Gly Tyr Leu Pro Met Ser Thr
            20                  25                  30

Thr Val Thr Trp Asp Thr Gly Ser Leu Asn Lys Asn Val Thr Thr Phe
        35                  40                  45

Pro Thr Thr Phe His Glu Thr Tyr Gly Leu His Ser Ile Val Ser Gln
    50                  55                  60
```

-continued

```
Val Thr Ala Ser Gly Glu Trp Ala Lys Gln Arg Phe Thr Cys Ser Val
65                  70                  75                  80

Ala His Xaa Glu Ser Thr Ala Ile Asn Lys Thr Phe Ser Ala
                85                  90


<210> SEQ ID NO 35
<211> LENGTH: 108
<212> TYPE: PRT
<213> ORGANISM: Canis familiaris
<220> FEATURE:
<221> NAME/KEY: misc_feature
<222> LOCATION: (81)..(81)
<223> OTHER INFORMATION: The 'Xaa' at location 81 stands for Lys, Arg,
      Thr, Met, Glu, Gly, Ala, Val, Gln, Pro, Leu, a stop codon, Trp,
      or Ser.
<220> FEATURE:
<221> NAME/KEY: misc_feature
<222> LOCATION: (82)..(82)
<223> OTHER INFORMATION: The 'Xaa' at location 82 stands for a stop
      codon, Trp, or Cys.
<220> FEATURE:
<221> NAME/KEY: misc_feature
<222> LOCATION: (136)..(136)
<223> OTHER INFORMATION: "n" stands for any nucleic acid
<220> FEATURE:
<221> NAME/KEY: misc_feature
<222> LOCATION: (413)..(414)
<223> OTHER INFORMATION: "n" stands for any nucleic acid
<220> FEATURE:
<221> NAME/KEY: misc_feature
<222> LOCATION: (451)..(451)
<223> OTHER INFORMATION: "n" stands for any nucleic acid
<220> FEATURE:
<221> NAME/KEY: misc_feature
<222> LOCATION: (460)..(462)
<223> OTHER INFORMATION: "n" stands for any nucleic acid
<220> FEATURE:
<221> NAME/KEY: misc_feature
<222> LOCATION: (500)..(500)
<223> OTHER INFORMATION: "n" stands for any nucleic acid
<220> FEATURE:
<221> NAME/KEY: misc_feature
<222> LOCATION: (530)..(530)
<223> OTHER INFORMATION: "n" stands for any nucleic acid
<220> FEATURE:
<221> NAME/KEY: misc_feature
<222> LOCATION: (568)..(568)
<223> OTHER INFORMATION: "n" stands for any nucleic acid
<220> FEATURE:
<221> NAME/KEY: misc_feature
<222> LOCATION: (847)..(849)
<223> OTHER INFORMATION: "n" stands for any nucleic acid
<220> FEATURE:
<221> NAME/KEY: misc_feature
<222> LOCATION: (853)..(853)
<223> OTHER INFORMATION: "n" stands for any nucleic acid
<220> FEATURE:
<221> NAME/KEY: misc_feature
<222> LOCATION: (1382)..(1382)
<223> OTHER INFORMATION: "n" stands for any nucleic acid
<220> FEATURE:
<221> NAME/KEY: misc_feature
<222> LOCATION: (1832)..(1832)
<223> OTHER INFORMATION: "n" stands for any nucleic acid

<400> SEQUENCE: 35

Cys Ala Leu Asn Phe Ile Pro Pro Thr Val Lys Leu Phe His Ser Ser
1               5                   10                  15

Cys Asn Pro Val Gly Asp Thr His Thr Thr Ile Gln Leu Leu Cys Leu
            20                  25                  30

Ile Ser Gly Tyr Val Pro Gly Asp Met Glu Val Ile Trp Leu Val Asp
        35                  40                  45
```

-continued

```
Gly Gln Lys Ala Thr Asn Ile Phe Pro Tyr Thr Ala Pro Gly Thr Lys
    50                  55                  60

Glu Gly Asn Val Thr Ser Thr His Ser Glu Leu Asn Ile Thr Gln Gly
65                  70                  75                  80

Xaa Xaa Val Ser Gln Lys Thr Tyr Thr Cys Gln Val Thr Tyr Gln Gly
                85                  90                  95

Phe Thr Phe Lys Asp Glu Ala Arg Lys Cys Ser Glu
            100                 105


<210> SEQ ID NO 36
<211> LENGTH: 107
<212> TYPE: PRT
<213> ORGANISM: Canis familiaris
<220> FEATURE:
<221> NAME/KEY: misc_feature
<222> LOCATION: (136)..(136)
<223> OTHER INFORMATION: "n" stands for any nucleic acid
<220> FEATURE:
<221> NAME/KEY: misc_feature
<222> LOCATION: (413)..(414)
<223> OTHER INFORMATION: "n" stands for any nucleic acid
<220> FEATURE:
<221> NAME/KEY: misc_feature
<222> LOCATION: (451)..(451)
<223> OTHER INFORMATION: "n" stands for any nucleic acid
<220> FEATURE:
<221> NAME/KEY: misc_feature
<222> LOCATION: (460)..(462)
<223> OTHER INFORMATION: "n" stands for any nucleic acid
<220> FEATURE:
<221> NAME/KEY: misc_feature
<222> LOCATION: (500)..(500)
<223> OTHER INFORMATION: "n" stands for any nucleic acid
<220> FEATURE:
<221> NAME/KEY: misc_feature
<222> LOCATION: (530)..(530)
<223> OTHER INFORMATION: "n" stands for any nucleic acid
<220> FEATURE:
<221> NAME/KEY: misc_feature
<222> LOCATION: (568)..(568)
<223> OTHER INFORMATION: "n" stands for any nucleic acid
<220> FEATURE:
<221> NAME/KEY: misc_feature
<222> LOCATION: (847)..(849)
<223> OTHER INFORMATION: "n" stands for any nucleic acid
<220> FEATURE:
<221> NAME/KEY: misc_feature
<222> LOCATION: (853)..(853)
<223> OTHER INFORMATION: "n" stands for any nucleic acid
<220> FEATURE:
<221> NAME/KEY: misc_feature
<222> LOCATION: (1382)..(1382)
<223> OTHER INFORMATION: "n" stands for any nucleic acid
<220> FEATURE:
<221> NAME/KEY: misc_feature
<222> LOCATION: (1832)..(1832)
<223> OTHER INFORMATION: "n" stands for any nucleic acid

<400> SEQUENCE: 36

Ser Asp Pro Arg Gly Val Ser Ser Tyr Leu Ser Pro Pro Ser Pro Leu
1               5                   10                  15

Asp Leu Tyr Val His Lys Ala Pro Lys Ile Thr Cys Leu Val Val Asp
            20                  25                  30

Leu Ala Thr Met Glu Gly Met Asn Leu Thr Trp Tyr Arg Glu Ser Lys
        35                  40                  45

Glu Pro Val Asn Pro Val Pro Leu Asn Lys Lys Asp His Phe Asn Gly
    50                  55                  60

Thr Ile Thr Val Thr Ser Thr Leu Pro Val Asn Thr Asn Asp Trp Ile
65                  70                  75                  80
```

-continued

```
Glu Gly Glu Thr Tyr Tyr Cys Arg Val Thr His Pro His Leu Pro Lys
                85                  90                  95

Asp Ile Val Arg Ser Ile Ala Lys Ala Pro Gly
            100                 105


<210> SEQ ID NO 37
<211> LENGTH: 108
<212> TYPE: PRT
<213> ORGANISM: Canis familiaris
<220> FEATURE:
<221> NAME/KEY: misc_feature
<222> LOCATION: (136)..(136)
<223> OTHER INFORMATION: "n" stands for any nucleic acid
<220> FEATURE:
<221> NAME/KEY: misc_feature
<222> LOCATION: (413)..(414)
<223> OTHER INFORMATION: "n" stands for any nucleic acid
<220> FEATURE:
<221> NAME/KEY: misc_feature
<222> LOCATION: (451)..(451)
<223> OTHER INFORMATION: "n" stands for any nucleic acid
<220> FEATURE:
<221> NAME/KEY: misc_feature
<222> LOCATION: (460)..(462)
<223> OTHER INFORMATION: "n" stands for any nucleic acid
<220> FEATURE:
<221> NAME/KEY: misc_feature
<222> LOCATION: (500)..(500)
<223> OTHER INFORMATION: "n" stands for any nucleic acid
<220> FEATURE:
<221> NAME/KEY: misc_feature
<222> LOCATION: (530)..(530)
<223> OTHER INFORMATION: "n" stands for any nucleic acid
<220> FEATURE:
<221> NAME/KEY: misc_feature
<222> LOCATION: (568)..(568)
<223> OTHER INFORMATION: "n" stands for any nucleic acid
<220> FEATURE:
<221> NAME/KEY: misc_feature
<222> LOCATION: (847)..(849)
<223> OTHER INFORMATION: "n" stands for any nucleic acid
<220> FEATURE:
<221> NAME/KEY: misc_feature
<222> LOCATION: (853)..(853)
<223> OTHER INFORMATION: "n" stands for any nucleic acid
<220> FEATURE:
<221> NAME/KEY: misc_feature
<222> LOCATION: (1382)..(1382)
<223> OTHER INFORMATION: "n" stands for any nucleic acid
<220> FEATURE:
<221> NAME/KEY: misc_feature
<222> LOCATION: (1832)..(1832)
<223> OTHER INFORMATION: "n" stands for any nucleic acid

<400> SEQUENCE: 37

Lys Arg Ala Pro Pro Asp Val Tyr Leu Phe Leu Pro Pro Glu Glu Glu
1               5                   10                  15

Gln Gly Thr Lys Asp Arg Val Thr Leu Thr Cys Leu Ile Gln Asn Phe
            20                  25                  30

Phe Pro Glu Asp Ile Ser Val Gln Trp Leu Arg Asn Asp Ser Pro Ile
        35                  40                  45

Gln Thr Asp Gln Tyr Thr Thr Thr Gly Pro His Lys Val Ser Gly Ser
    50                  55                  60

Arg Pro Ala Phe Phe Ile Phe Ser Arg Leu Val Asp Trp Glu Gln Lys
65                  70                  75                  80

Asn Lys Phe Thr Cys Gln Val Val His Glu Ala Leu Ser Gly Ser Arg
                85                  90                  95

Ile Leu Gln Lys Trp Val Ser Lys Thr Pro Gly Lys
            100                 105
```

-continued

```
<210> SEQ ID NO 38
<211> LENGTH: 213
<212> TYPE: DNA
<213> ORGANISM: Canis familiaris
<220> FEATURE:
<221> NAME/KEY: CDS
<222> LOCATION: (1)..(213)

<400> SEQUENCE: 38

gaa ggc atg aac ctg acc tgg tac cgg gag agc aaa gaa ccc gtg aac       48
Glu Gly Met Asn Leu Thr Trp Tyr Arg Glu Ser Lys Glu Pro Val Asn
1               5                   10                  15

ccg gtc cct ttg aac aag aag gat cac ttc aat ggg acg atc aca gtc       96
Pro Val Pro Leu Asn Lys Lys Asp His Phe Asn Gly Thr Ile Thr Val
            20                  25                  30

acg tct acc ctg cca gtg aac acc aat gac tgg atc gag ggc gag acc      144
Thr Ser Thr Leu Pro Val Asn Thr Asn Asp Trp Ile Glu Gly Glu Thr
        35                  40                  45

tac tat tgc agg gtg acc cac ccg cac ctg ccc aag gac atc gtg cgc      192
Tyr Tyr Cys Arg Val Thr His Pro His Leu Pro Lys Asp Ile Val Arg
    50                  55                  60

tcc att gcc aag gcc cct ggt                                          213
Ser Ile Ala Lys Ala Pro Gly
65                  70


<210> SEQ ID NO 39
<211> LENGTH: 71
<212> TYPE: PRT
<213> ORGANISM: Canis familiaris

<400> SEQUENCE: 39

Glu Gly Met Asn Leu Thr Trp Tyr Arg Glu Ser Lys Glu Pro Val Asn
1               5                   10                  15

Pro Val Pro Leu Asn Lys Lys Asp His Phe Asn Gly Thr Ile Thr Val
            20                  25                  30

Thr Ser Thr Leu Pro Val Asn Thr Asn Asp Trp Ile Glu Gly Glu Thr
        35                  40                  45

Tyr Tyr Cys Arg Val Thr His Pro His Leu Pro Lys Asp Ile Val Arg
    50                  55                  60

Ser Ile Ala Lys Ala Pro Gly
65                  70
```

SPECIFIC BINDING PROTEINS FOR TREATING CANINE ALLERGY

This application is a continuation-in-part of application U.S. Ser. No. 09/058,331, filed Apr. 9, 1998, now abandoned which is incorporated herein in its entirety.

FIELD OF THE INVENTION

This invention concerns peptides. More particularly, the invention concerns compositions for administration to dogs, which actively provide immunity to the dog's immunoglobulin E molecules.

BACKGROUND ART

It is estimated that up to 30% of all dogs suffer from allergies or allergy-related skin disorders. Specifically, allergic dermatitis has been estimated to affect between 3 and 15% of the entire canine population. Given the prevalence of allergies in dogs, there is a need to develop methods and compositions to properly diagnose and treat canine allergies.

The substances most likely to cause an allergic reaction vary from species to species. Common canine allergens include fleas, pollens, molds and dust. Allergy to fleas is believed to be the most common dog allergy. Typically, a flea's saliva is the allergen, and a single fleabite can cause substantial itching. An additional form of allergy in dogs is termed atopy. Atopy is a condition where a dog is allergic to inhalants such as pollens, molds or microscopic mites such as are found in house dust.

Antibody molecules play a role in allergic manifestations. In mammals, antibody molecules are classified into various isotypes referred to as IgA, IgD, IgE, IgG, and IgM. Antibody molecules consist of both heavy and light chain components. The heavy chains of molecules of a given isotype have extensive regions of amino acid sequence homology, and conversely have regions of difference from antibodies belonging to other isotypes. The shared regions of the heavy chains provide members of each isotype with common abilities to bind to certain cell surface receptors or to other macromolecules, such as complement. These heavy chain regions, therefore, serve to activate particular immune effector functions. Accordingly, separation of antibody molecules into isotypes serves to separate the antibodies according to a set of effector functions that they commonly activate.

In humans and dogs, immunoglobulin E (hereinafter IgE) is involved in allergy. Thus, IgE is the antibody type that is understood to be an important mediator of allergic responses, including Type I immediate hypersensitivity.

IgE molecules bind to mast cells and basophils. This binding occurs when the Fc region of the IgE molecule is bound to Fc receptors on the mast cells. When such bound IgE antibodies then bind to an allergen, the allergen cross-links multiple IgE antibodies on the cell surface. This cross-linking mediates Type I immediate hypersensitivity reactions and causes release of histamines and other molecules that produce symptoms associated with allergy.

Monoclonal antibodies having different degrees of sensitivity to canine IgE and IgG have been identified. (DeBoer, et al. Immunology and Immunopathology 37, 183–199 (1993).) DeBoer, et al. identified several monoclonal antibodies which had cross reactivity between IgG and IgE. (See, e.g., DeBoer, et al., Table 4 and accompanying text.) Three monoclonal antibodies (A5, D9, and B3) were identified by DeBoer et al., as having some affinity for canine IgE. Of the monoclonal antibodies identified in DeBoer et al., antibody D9 appeared to have the greatest degree of neutralization of Prausnitz-Kustner reactivity for atopic dog serum. In the context of canine allergy, DeBoer et al. proposed use of their monoclonal antibodies (MAbs) in the use of antigen-specific IgE ELISA, and for quantifying canine IgE. Additionally, they proposed use of their MAbs for immunostaining of Western Blot assays, to evaluate the molecular specificity of IgE antibodies, as well as for in vitro studies on degranulation of mast cells.

In humans the serum level of total IgE is diagnostic of allergic disease. To explore the possibility that the serum level of IgE might also be diagnostic of allergy in dogs, several studies were performed. (Hill and DeBoer Am. J. Yet. Res., (July 1994) 55(7), 944–48). Publications following the DeBoer article used a monoclonal antibody designated D9 in an ELISA assay having the following configuration: D9 was bound to a substrate, antibodies were captured by D9 and then D9 having a marker was used to flag the captured antibody. The Hill and DeBoer ELISA was used to establish the total amount of IgE in canine serum in an effort to diagnose canine allergy. In contrast to humans, the quantity of IgE determined to exist in canine circulation was of no use whatsoever in the diagnosis of allergy in dogs. (See, e.g., Abstract and Discussion Sections of Hill and DeBoer) This finding was in direct contrast to the situation in human immunology.

This divergent diagnostic result based on levels of IgE in humans compared to such levels in dogs, points out the difficulty of any attempt to correlate data between animals of two different genera. This difficulty is further exacerbated by the fact that dogs can be allergic to a different set of antigens than humans are. Fleas, for instance, are a severe problem for dogs, but not humans. Furthermore, in instances where dogs and humans appear to be allergic to the same allergen extract, studies by doctors Esch and Greer of Greer Laboratories, have indicated that the specific allergens in an allergen extract which produce canine disease are not necessarily the same allergens that produce disease in humans. For example, it is known that the immunodominant components of dust mite extracts are different in dogs than in humans.

The genomic sequences encoding human and murine IgE heavy chain constant region are known (For example, see Ishida et al., "The Nucleotide Sequence of the Mouse Immunoglobulin E Gene: Comparison with the Human Epsilon Gene Sequence", EMBO Journal 1,1117–1123 (1982). A comparison of the human and murine genes shows that they possess 60% homology within exons, and 45–50% homology within introns, with various insertions and deletions.

Patel et al. published the nucleotide and predicted amino acid sequence for exons 1–4 of the heavy chain constant region of canine IgE in the article entitled "Sequence of the Dog Immunoglobulin Alpha and Epsilon Constant Region Genes," Immunogenetics 41, 282–286 (Mar. 22, 1995). The complete sequence of the canine IgE heavy chain constant region, with membrane bound portions encoded by exons 5 and 6 are disclosed in copending applications Ser. No. 08/800,698 filed Feb. 14, 1997, Ser. No. 09/146,400 filed Sep. 3, 1998, and Ser. No. 09/146,617 filed Sep. 3, 1998.

Because IgE is believed to mediate allergic symptoms, it may be desirable to decrease IgE levels as a mechanism for alleviating allergic symptoms. However, a patient's own IgE molecules are self-proteins, and immune responses to such proteins are usually suppressed. The suppression of immune responses to self-proteins, i.e., tolerance to self-antigens, is hypothesized to occur in a number of ways.

The current hypothesis for suppression of T cells directed to self-antigens, involves an induction of “clonal deletions” of such T cells in the thymus, whereby T cell receptors which might recognize self-peptides in association with MHC molecules are eliminated, and only those which recognize foreign peptide and MHC molecules are allowed to expand. In addition, suppressor T cells may also exist which prevent the induction of immune responses to self-proteins.

In contrast to the situation with T cells, it is believed that there are many B cells which express receptors (i.e., surface immunoglobulin) for self-proteins, and that the reason these cells do not produce antibodies to self-proteins is because the T cells required for the antigen presentation to the B cell are normally missing.

A B cell which recognizes epitopes (antigen-binding sites) on a patient’s own IgE antibodies is capable of generating antibodies, generally IgG, directed to this self-antigen, i.e., IgE. The existence of such B cells, therefore, presents a unique opportunity to induce the production of auto-antibody responses. There is an unmet need for such antibodies in order to treat allergic disease.

The hypothesis regarding “antigen presentation” involves: the recognition of antigen by surface immunoglobulin on the B cell, the internalization and processing of this antigen, the association of peptides derived from the antigen with MHC molecules expressed on the surface of the B cell, and then, the recognition of the associated antigen peptide and MHC molecules by a particular T cell. The T-cell:B-cell interaction then leads to signal transduction in both cells and the synthesis and elaboration of soluble cytokines which eventually result in antibody production by the B cell.

Thus, in most circumstances, only when an antigen is foreign does an immune response occur; otherwise the internalization and processing of self-proteins would regularly lead to the presentation of self peptide-MHC complexes to T cells and thereby lead to autoimmune antibodies.

Therefore, in order to induce an antibody response to a self-peptide, such as IgE, the immune system must be manipulated so as to allow an auto-reactive B cell to become an antibody-secreting B cell. There is an unmet need to manipulate the immune system in this way, particularly in the context of allergic disease.

In general, there are several known approaches for generating antibodies to peptide antigens. For example, multiple antigenic peptides (MAPs), introduced by Dr. James Tam (Tam, J. P., (1988) Proc. Natl. Acad. Sci. U.S.A. 85, 5409–5413), have demonstrated several advantages for inducing anti-peptide antibodies. The MAP approach is an improved alternative to the conventional technique of conjugating a peptide antigen to a protein carrier. One of the primary limitations associated with the use of protein carriers is the large mass of the carrier relative to the attached peptide antigen. This relative size disparity may result in a low ratio of anti-peptide antibodies compared to anti-carrier antibodies. MAPs typically have 4 or 8 peptide arms branching out from a lysine core matrix as depicted in FIG. 1A–B. The peptide antigen is conjugated to each arm. Thus there is a much higher ratio of antigen to carrier molecule in a MAP system compared to traditional protein conjugation. This design maximizes the concentration of the antigen for a specific immunogenic response. Moreover, the central lysine core of the MAP-peptide has been shown to be non-immunogenic. (Tam, J. P., Proc. Natl. Acad. Sci. U.S.A. 85, 5409–5413 (1988); Posnett, D. N., McGrath, H., and Tam, J. P., J. Biol. Chem. 263, 1719–1725 (1988)) Therefore, antibodies induced to MAP-peptides are a direct response to the antigen. Accurate knowledge of the chemical composition, structure, and quantity of the peptide prior to immunization is possible by directly synthesizing the antigen onto the branching lysine core. Also, because the MAP approach removes the need to conjugate peptides to carrier proteins, which may alter the antigenic determinants, chemical ambiguity is eliminated. Thus MAPs are believed to induce antibody responses of high purity, increased avidity, accurate chemical definition, and improved safety.

Fmoc MAP resins (available from Applied Biosystems, Foster City, Calif.) are Fmoc-compatible resins connected to a small core matrix of branching lysine residues. The core matrix comprises several levels of lysine residues attached to the previous lysine at both the N-α and N-ε amino groups, as depicted in FIGS. 1A–B.

MAP-peptides used in experimental vaccine design have elicited high titers of anti-peptide antibodies that recognize the native protein. (Tam, J. P., (1988) Proc. Natl. Acad. Sci. U.S.A. 85, 5409–5413; Posnett, D. N., McGrath, H., and Tam, J. P., (1988) J. Biol. Chem. 263, 1719–1725; Auriault, C., Wolowczuk, I., Gras-Masse, H., Maguerite, M., Boulanger, D., Capron, A., and Tartar, A., (1991) Peptide Res.4, 6–11). Additionally, increased sensitivity and reliability of antibody-antigen interactions in solid-phase immunoassays have been observed with MAP-peptides due to enhanced coating capacity and avidity. (Tam, J. P., and Zavala, F., (1989) J. Immunol. Meth., 124, 53–61).

An additional approach that is known to be useful for generating antibodies to peptide antigens involves placing multiple copies of peptides on the surface of plant virus particles. EPICOAT™ technology (Axis Genetics plc, Cambridge, England) is one such example. The EPICOAT™ technology is based on chimeric virus particle (CVP) technology that utilizes the recombinant genetic modification of plant viruses.

The EPICOAT™ technology involves insertion of a small portion of a foreign protein (a peptide) into a plant virus in such a way that multiple copies of the peptide are displayed on the surface of the virus particle. The EPICOAT™ technology is currently based on the cow pea mosaic virus (CPMV) a plant virus that infects the cow pea plant, also known as the “black-eyed” bean. The unmodified CPMV particle is icosahedral, and about twenty-eight nanometers (nm.) in diameter. CPMV particles are composed of two proteins, referred to as the large and small coat proteins. Studies have revealed a site within the small coat protein which allows presentation of a foreign peptide in a prominent position on the virus surface, whereby up to sixty copies of a particular peptide can be presented on each virus particle.

With the EPICOAT™ technology, DNA copies of the plant virus’s genetic material are used. A minute quantity of the DNA encoding the virus protein, including the inserted foreign peptide, is applied to the leaves of young cow pea plant, along with an abrasive powder. Upon gentle rubbing, DNA enters the leaves and utilizes the plant’s own cellular mechanisms to initiate generation of functional virus particles. The virus replicates within the inoculated leaves and spreads throughout the growing plant.

After two to three weeks, leaf material containing large quantities of the virus is harvested. Chimeric virus particles (CVPs) are isolated by centrifugation and selective precipitation of homogenized plant material. Between 1 to 2 grams of CVPs can be obtained per kilogram fresh weight of leaf material. Cow pea plants are readily grown in abundance in controlled environments, allowing generation of large quantities of CVPs.

It has been reported that peptides of up to thirty-six amino acids in size have been successfully incorporated into CVPs. The resulting particles are extremely robust with a thermal inactivation point of 65° C. The CVPs have been shown to withstand acidic pH as well as protein degrading enzymes. It has been reported that the expressed peptides are capable of eliciting specific immune responses in animals. It has been hypothesized that surface presentation of peptides may enhance the recognition by the host immune system, and may provide a route for development of recombinant subunit vaccines and immuno-therapeutics.

DISCLOSURE OF THE INVENTION

Disclosed is a specific binding protein which specifically binds to native canine free or B cell-bound IgE exon 3, and which does not bind to IgE exon 3 when the IgE is bound to receptor on a mast cell. The surface-bound IgE can be IgE expressed on the surface of a canine B cell.

Disclosed is a specific binding protein which specifically binds to an isolated and purified peptide comprising a leucine positioned two peptide bonds away from a tyrosine-arginine pair; e.g., SEQ ID NO:1 leucine-blank-blank-tyrosine-arginine, SEQ ID NO:2 tyrosine-arginine-blank-blank-leucine, or SEQ ID NO:3 leucine-blank-blank-tyrosine-arginine-blank-blank-leucine. The peptide can consist of from 5 to 71 amino acids.

Disclosed is an antibody which binds to a defined epitope and which is raised to an isolated and purified peptide comprising an amino acid sequence, or a conservative variant thereof, which comprises: SEQ ID NO:4 Thr-Leu-Leu-Glu-Tyr-Arg-Met; also disclosed is a recombinant binding molecule which specifically binds to the defined epitope bound by the antibody.

Disclosed is an antibody which binds to a defined epitope and which is raised to an isolated and purified peptide comprising an amino acid sequence, or a conservative variant thereof, which comprises: SEQ ID NO:5 Gly-Met-Asn-Leu-Thr-Trp-Tyr-Arg-Glu-Ser-Lys; also disclosed ii a recombinant binding molecule which specifically binds to the defined epitope bound by the antibody.

Also disclosed is a specific binding protein which is raised to a multiply antigenic peptide comprising multiple copies of an isolated and purified peptide which comprises a leucine positioned two peptide bonds away from a tyrosine-arginine pair; the specific binding protein specifically binds to a defined epitope. The isolated and purified peptide can be from 5–71 amino acids. Also disclosed is a recombinant binding molecule which specifically binds to the defined epitope bound by the binding protein.

Disclosed is a specific binding protein which specifically binds to an isolated and purified peptide comprising a cysteine positioned two peptide bonds away from a proline-histidine pair positioned three peptide bonds from a cysteine. The peptide can have the form: SEQ ID NO:6 cysteine-blank-blank-proline-histidine-blank-blank-blank-cysteine. The cysteines may form a covalent bond through a reduction reaction, cyclizing the peptide and becoming cystine. The peptide can comprise from 9 to 71 amino acids.

Disclosed is an antibody that binds to a defined epitope and which is raised to an isolated and purified peptide that has the amino acid sequence, or a conservative variant thereof, which comprises: SEQ ID NO:7 serine-valine-threonine-leucine-cysteine-proline-asparagine-proline-histidine-isoleucine-proline-methionine-cysteine-glycine-glycine-glycine. The cysteines may form a covalent bond through a reduction reaction, cyclizing the peptide and becoming cystine. Also disclosed is a recombinant binding molecule that specifically binds to the defined epitope bound by the antibody.

Disclosed is an antibody that binds to a defined epitope and which is raised to an isolated and purified peptide that has the amino acid sequence, or a conservative variant thereof, which comprises: SEQ ID NO:8 serine-alanine-cysteine-proline-asparagine-proline-histidine-asparagine-proline-tyrosine-cysteine-glycine-glycine-glycine. The cysteines may form a covalent bond through a reduction reaction, cyclizing the peptide changing the amino acid to cystine. Also disclosed is a recombinant binding molecule that specifically binds to the defined epitope bound by the antibody.

Disclosed is a specific binding protein that specifically binds to an isolated and purified peptide comprising a cysteine positioned one peptide bond from a proline-histidine pair, positioned one peptide bond from a proline, positioned two peptide bonds from a cysteine; the peptide can have the form: SEQ ID NO:9 cysteine-blank-proline-histidine-blank-proline-blank-blank-cysteine. The cysteines may form a covalent bond through a reduction reaction, cyclizing the peptide and becoming cystine. The peptide can comprise from 9 to 71 amino acids.

Disclosed is an antibody that binds to a defined epitope and which is raised to an isolated and purified peptide that has the amino acid sequence, or a conservative variant thereof, which comprises: SEQ ID NO:10 serine-alanine-cysteine-histidine-proline-histidine-leucine-proline-lysine-serine-cysteine-glycine-glycine-glycine. The cysteines may form a covalent bond through a reduction reaction, cyclizing the peptide and becoming cystine. Also disclosed is a recombinant binding molecule that specifically binds to the defined epitope bound by the antibody.

Specific binding proteins in accordance with the invention can be antibodies, either polyclonal or monoclonal. For example the monoclonal antibody can be 8H.8 or 15A.2. The antibody in accordance with the invention will bind a defined epitope; also disclosed are recombinant binding molecules which specifically binds to the defined epitope bound by an antibody in accordance with the invention.

Also disclosed is a method for treatment or prophylaxis for canine allergy, said method comprising: providing a specific binding molecule in accordance with the invention; and, administering the provided binding molecule to a dog. The method can comprise a step of mixing the provided binding molecule with a diluent prior to the administering step, and wherein the administering step comprises administering the mixture of the molecule and the diluent. A step of administering a booster dose of the binding molecule can follow the administering step.

DEFINITIONS

Amino Acids:
AMINO ACID ABBREVIATIONS

| Amino Acid | One-Letter Symbol | Three-Letter Symbol |
|---|---|---|
| alanine | A | ala |
| arginine | R | arg |

-continued

| Amino Acids: AMINO ACID ABBREVIATIONS | | |
|---|---|---|
| Amino Acid | One-Letter Symbol | Three-Letter Symbol |
| asparagine | N | asn |
| aspartic acid | D | asp |
| cysteine | C | cys |
| glutamic acid | E | glu |
| glutamine | Q | gln |
| glycine | G | gly |
| histidine | H | his |
| isoleucine | I | ile |
| leucine | L | leu |
| lysine | K | lys |
| methionine | M | met |
| phenylalanine | F | phe |
| proline | P | pro |
| serine | S | ser |
| threonine | T | thr |
| tryptophan | W | trp |
| tyrosine | Y | tyr |
| valine | V | val |

cDNA clone: A duplex DNA sequence representing an RNA, carried in a cloning vector.

Cloning: The selection and propagation of a single DNA species.

Cloning Vector: A plasmid, phage DNA or other DNA sequence, able to replicate in a host cell and capable of carrying exogenously added DNA sequence for purposes of amplification or expression of the added DNA sequence.

Codon: A triplet of nucleotides that represents an amino acid or termination signal.

Conservative variants: Conservative variants of nucleotide sequences include nucleotide substitutions that do not result in changes in the amino acid sequence encoded by such nucleotides, as well as nucleotide substitutions that result in conservative amino acid substitutions, e.g., amino acid substitutions which do not substantially affect the character of the polypeptide translated from said nucleotides. For example, the character of a peptide derived from IgE is not substantially affected if the substitutions do not preclude specific binding of the peptide to canine IgE receptor or other canine IgE binding ligands.

Conservative variants of amino acid sequences include amino acid substitutions or deletions that do not substantially affect the character of the variant polypeptide relative to the starting peptide. For example, polypeptide character is not substantially affected if the substitutions or deletions do not preclude specific binding of the variant peptide to a specific binding partner of the starting peptide. The term mimotope refers to a conservative variant of an amino acid sequence, to which antibody specificity has been raised. The mimotope comprises a variant of the epitope of the starting peptide such that it is able to bind antibodies that cross-react with the original epitope.

DNA Sequence: A linear series of nucleotides connected one to the other by phosphodiester bonds between the 3' and 5' carbons of adjacent pentoses.

Expression: The process undergone by a structural gene to produce a polypeptide. It is a combination of transcription and translation.

Expression Control Sequence: A DNA sequence of nucleotides that controls and regulates expression of structural genes when operatively linked to those genes.

Exon: A contiguous region of DNA encoding a portion of a polypeptide. Reference to any exon, e.g. "DNA sequence of exon 6", refers to the complete exon or any portion thereof.

Genome: The entire DNA of a substance. It includes inter alia the structural genes encoding for the polypeptides of the substance, as well as operator, promoter and ribosome binding and interaction sequences such as the Shine-Dalgarno sequences.

Nucleotide: A monomeric unit of DNA or RNA consisting of a sugar moiety (pentose), a phosphate, and a nitrogenous heterocyclic base. The four DNA bases are adenine ("A"), guanine ("G"), cytosine ("C") and thymine ("T"). The four RNA bases are A, G, C and uracil ("U"). A and G are purines, and C, T, and U are pyrimidines.

Phage or Bacteriophage: Bacterial virus, many of which include DNA sequences encapsidated in a protein envelope or coat ("capsid").

Plasmid: An autonomous self-replicating extrachromosomal circular DNA.

Polymerase Chain Reaction (PCR): A method of amplifying a target DNA sequence contained in a mixture of DNA sequences, by using oligonucleotide primers that flank the target DNA sequence for repeated cycles of DNA synthesis of the target DNA sequence.

Polypeptide: A linear series of amino acids connected one to the other by peptide bonds between the a-amino and carboxyl groups of adjacent amino acids.

Reading Frame: The grouping of codons during translation of mRNA into amino acid sequences. For example, the sequence GCTGGTGTAAG may be translated in three reading frames or phases, each of which affords a different amino acid sequence:

GCT GOT TGT AAG-Ala-Gly-Cys-Lys

G CTG GTT GTA AG-Leu-Val-Val

GC TGG TTG TAA A-Trp-Leu-(STOP).

Recombinant DNA Molecule: A hybrid DNA sequence comprising at least two nucleotide sequences, the first sequence not normally being found together in nature with the second.

Specific binding: Binding of one substance to another at greater binding affinity than background binding. Two substances that exhibit specific binding are referred to as specific binding partners, or as a specific binding pair. An antibody and its antigen are one example of a specific binding pair.

Specific Binding Molecule: A molecule that exhibits specific binding to its corresponding binding partner to form a specific binding pair. As used herein, this definition of specific binding molecule covers monoclonal and polyclonal antibodies, antigen-binding fragments of these antibodies, hybrid antibodies, single-chain antibodies, and recombinant molecules capable of specific binding to a ligand.

Structural Gene: A DNA sequence that encodes through its template or messenger RNA ("mRNAII) a sequence of amino acids characteristic of a specific polypeptide.

Transcription: Synthesis of RNA on a DNA template.

Translation: Synthesis of peptides on the mRNA template.

DESCRIPTION OF FIGURES

FIG. 6 depicts the amino acid sequences of the New England Biolabs PhDc7c phage display library that were bound by the monoclonal antibody 15A.2. These sequences (SEQ ID NOS:11 and 18–25) are shown in alignment with the protein sequence of canine IgE (SEQ ID NO:26).

FIG. 7 depicts the alignment of the 15A.2 binding region from seven different mammals: dog (SEQ ID NO:26), human (SEQ ID NO:27), green monkey (SEQ ID NO:28), cat (SEQ ID NO:29), swine (SEQ ID NO:30), mouse (SEQ ID NO:31) and horse (SEQ ID NO:32).

MODES FOR CARRYING OUT INVENTION

Figure 1A:
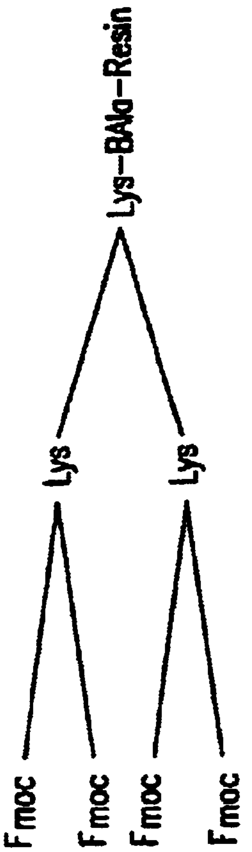
FIG. 1A depicts the core structure of a MAP protein with four arms, i.e., a 4-MAP protein.
Figure 1B:
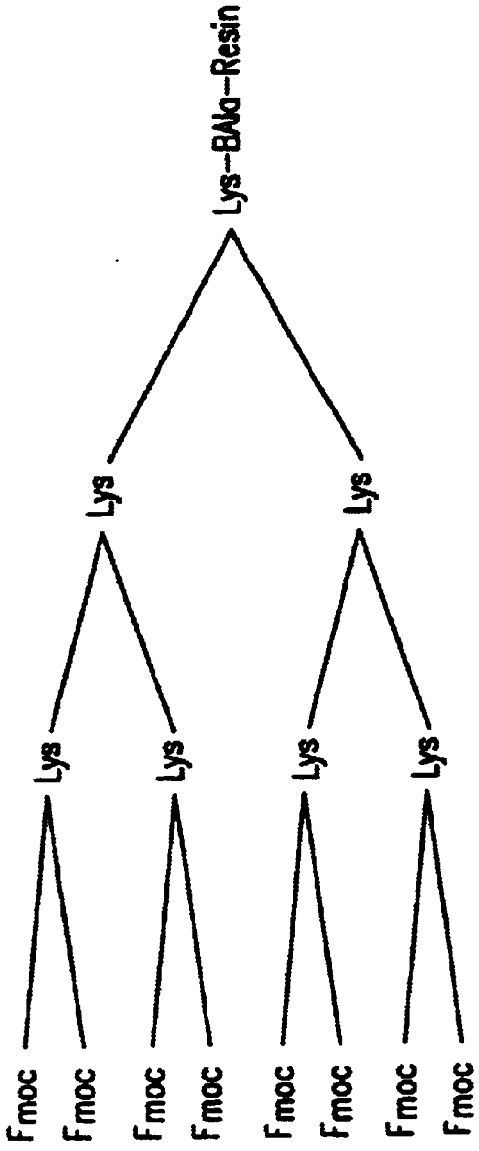
FIG. 1B depicts the core structure of a MAP protein with eight arms, i.e., an 8-MAP protein.

Proposed Mechanism of Action of Anti-IgE Monoclonal Antibodies in Causing Persistent Serum IgE Depletion A hypothesis in accordance with the present invention is that anti-IgE monoclonal antibodies affect IgE levels by directly binding with the resident circulating IgE, after which the bound complex is removed from the circulation.

Moreover, it is hypothesized that anti-IgE monoclonal antibodies affect IgE levels by interfering with the production of new IgE by B-cells. Memory B-cells, cells that upon interacting with antigen and T-cell become antibody producing cells (i.e., “memory IgE B-cells”), are involved in replenishing serum IgE, and these cells contain IgE as their cell surface receptors. Thus, it is possible that anti-IgE monoclonal antibodies bind to the IgE on these antibody producing cells and interfere with their function, such as by down-regulation or by one or more mechanisms which lead to cell destruction. Two general ways have been proposed for how the binding of a monoclonal antibody to a memory B cell might interfere with production of IgE.

First, activation of a memory B cell, may also require the involvement of a surface IgE-binding factor designated CD23. Binding of certain monoclonal antibodies to the cell surface IgE may preclude CD23 binding, and may thus lead to an inability to mount an IgE response.

Second, IgE antibody production by a memory IgE B cell may be reduced or eliminated by binding of a monoclonal antibody that is directed against, or blocks, the receptor for the IgE molecule which is located on the surface of the memory B cell.

In the absence of a monoclonal antibody that leads to memory IgE B cell elimination or inactivation, however, it would be expected that the memory IgE B-cells would be replenished, leading to the eventual replenishment of circulating IgE.

The serum levels of IgE are elevated in patients experiencing allergic disease. As disclosed herein, when antibodies were generated that specifically bind to a species’ IgE, and these antibodies were administered to a patient who is a member of the species (“passive immunization”), that patient’s serum levels of IgE declined. As appreciated by one of ordinary skill in the art, the specific binding proteins in accordance with the invention are administered in pharmacologically accepted dosages, and can be administered with suitable biocompatible diluents. Also disclosed herein are a method and related compositions that serve to induce a response to a self-peptide, such as an IgE molecule, whereby the immune system is manipulated so as to allow an auto-reactive B cell to become an antibody-secreting B cell (“active immunization”).

Receptors are present on mast cells that bind to IgE from the circulation. When IgE has become bound to the receptors on mast cells, the IgE molecules can become crosslinked. Upon cross-linking these IgE molecules, the mast cell is induced to release histamine. Histamine is an agent that induces the manifestation of allergic symptoms. Generally, cross-linking occurs by binding of the IgE molecules to an antigen, e.g., an allergen. However, a monoclonal antibody that binds to IgE could serve as a means for cross-linking IgE which has become bound to the surface of mast cells.

For allergic individuals, if anti-IgE antibodies were present in circulation, it becomes easy to envisage that the binding of such auto-anti-IgE to IgE molecules on mast cells could serve to cross-link the IgE molecules on those cells and exacerbate an ongoing allergic response even in the absence of allergen. This occurrence is clearly undesirable in the context of allergy treatment. An antibody that achieved this function would therefore not be preferred for use as a therapeutic in accordance with the invention. Therefore, an antibody that achieves such crosslinking is disadvantageous, and is not preferred in accordance with the invention.

Two approaches exist for producing monoclonal antibodies which target IgE, but which do not cross-link IgE molecules which have become bound to a mast cell. The first is to produce monoclonal antibodies that are directed to an epitope of an IgE molecule that is only accessible when the IgE is in circulation. Since the monoclonal antibody can only bind to IgE when it is in circulation, it will not be able to bind to IgE that has become bound to the surface of a mast cell.

An alternative approach for producing anti-IgE antibodies has been hypothesized by Stanworth et al, e.g., U.S. Pat. No. 5,601,821 issued Feb. 11, 1997. The antibodies of Stanworth are disclosed to cross-link IgE on mast cells, but in a manner that does not induce histamine release. Stanworth has disclosed an epitope of the human IgE molecule which must be available or accessible after IgE molecules have become cross-linked on the surface of a mast cell, in order for the mast cell to release histamine. Thus, Stanworth disclosed an antibody that binds to that particular epitope. Accordingly, monoclonal antibodies that are directed to this IgE epitope will serve to cross-link the IgE, but will not permit the mast cell to release histamine.

The approach followed in accordance with the present invention is the development of antibodies, either ex vivo monoclonal or in vivo anti-self antibodies, directed to epitopes which are accessible on circulating IgE but which are not accessible when such IgE becomes bound to a mast cell.

Passive Immunity

Monoclonal Antibodies 15A.2 and 8H.8

Monoclonal antibody 15A.2 binds to canine IgE. The 15A.2 monoclonal antibody was derived by immunizing mice with affinity-purified canine IgE. The epitope bound by 15A.2 is conformational, not linear. As indicated by data depicted in FIG. 2, 15A.2 did not bind to the IgE receptor; nor did it bind to IgE when bound to receptor. However, 15A.2 exhibited affinity for free IgE. It binds to recombinant canine exon 3 fusion proteins in an enzyme linked immunosorbent assay (ELISA) and by Western blot, but not to other recombinant canine IgE fusion proteins.

Characterization experiments of the 15A.2 monoclonal antibody showed that 15A.2 did not bind to IgE that was already bound by the IgE receptor on mast cells. Thus, it appeared that access to the epitope bound by 15A.2 was hindered by IgE binding to the Fc receptor on mast cells. Accordingly, 15A.2 will not crosslink IgE bound to mast cells. This finding was demonstrated by binding studies with a recombinant receptor discussed herein.

Monoclonal antibody 8H.8 also binds to canine IgE. The 8H.8 monoclonal antibody was derived by immunizing mice with a shortened version of exon 3 of the canine IgE molecule, designated exon 3a. Exon 3a contains the C-terminal 71 amino acids of the full length exon 3. See SEQ ID NOs:33–39, and in particular SEQ ID NO:38 and 39. Previous studies (data not presented herein) had shown that immunizing mice with the full length exon 3 did not generate antibodies having specificity such as that ultimately found with the 8H.8 antibody.

Figure 2:
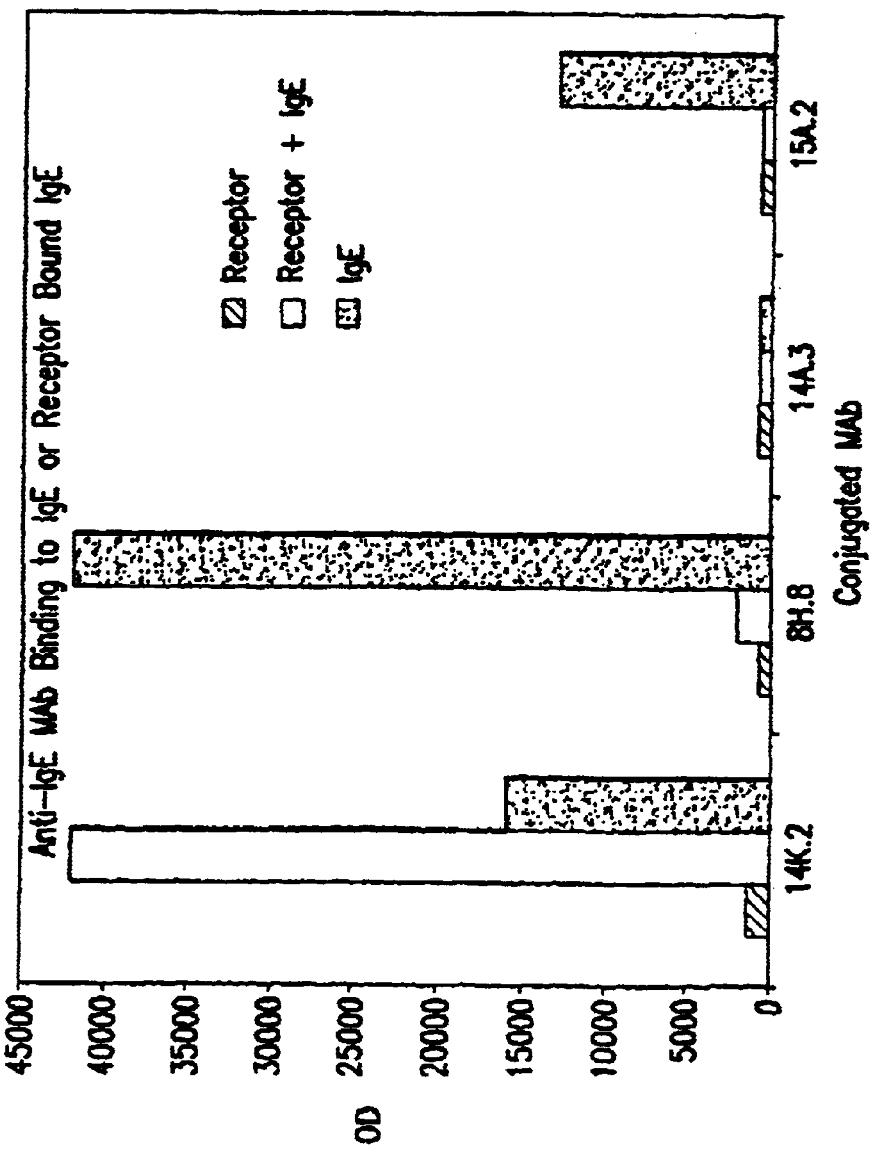
FIG. 2 depicts data comparing the binding characteristics of several monoclonal antibodies to surface bound IgE (e.g., analogous to IgE expressed on the surface of B cells); IgE receptor (e.g., analogous to the Fc receptor on mast cells); and to a combination of IgE when bound by the IgE receptor. Thus each component assayed was immobilized on a solid surface.

Characterization experiments of the 8H.8 monoclonal antibody showed that, unlike monoclonal antibodies derived by immunization with all other recombinant IgE sequences, 8H.8 would also bind to native canine IgE. Additionally, like 15A.2 and as depicted in FIG. 2, it was found that 8H.8 did not bind to IgE that was already bound by the IgE receptor on mast cells. Thus, it appeared that access to the epitope bound by 8H.8 was also hindered by IgE binding to the Fc receptor on mast cells. As a result, 8H.8 will not crosslink IgE bound to mast cells. This finding was demonstrated by binding studies with a recombinant receptor discussed herein.

Figure 3:
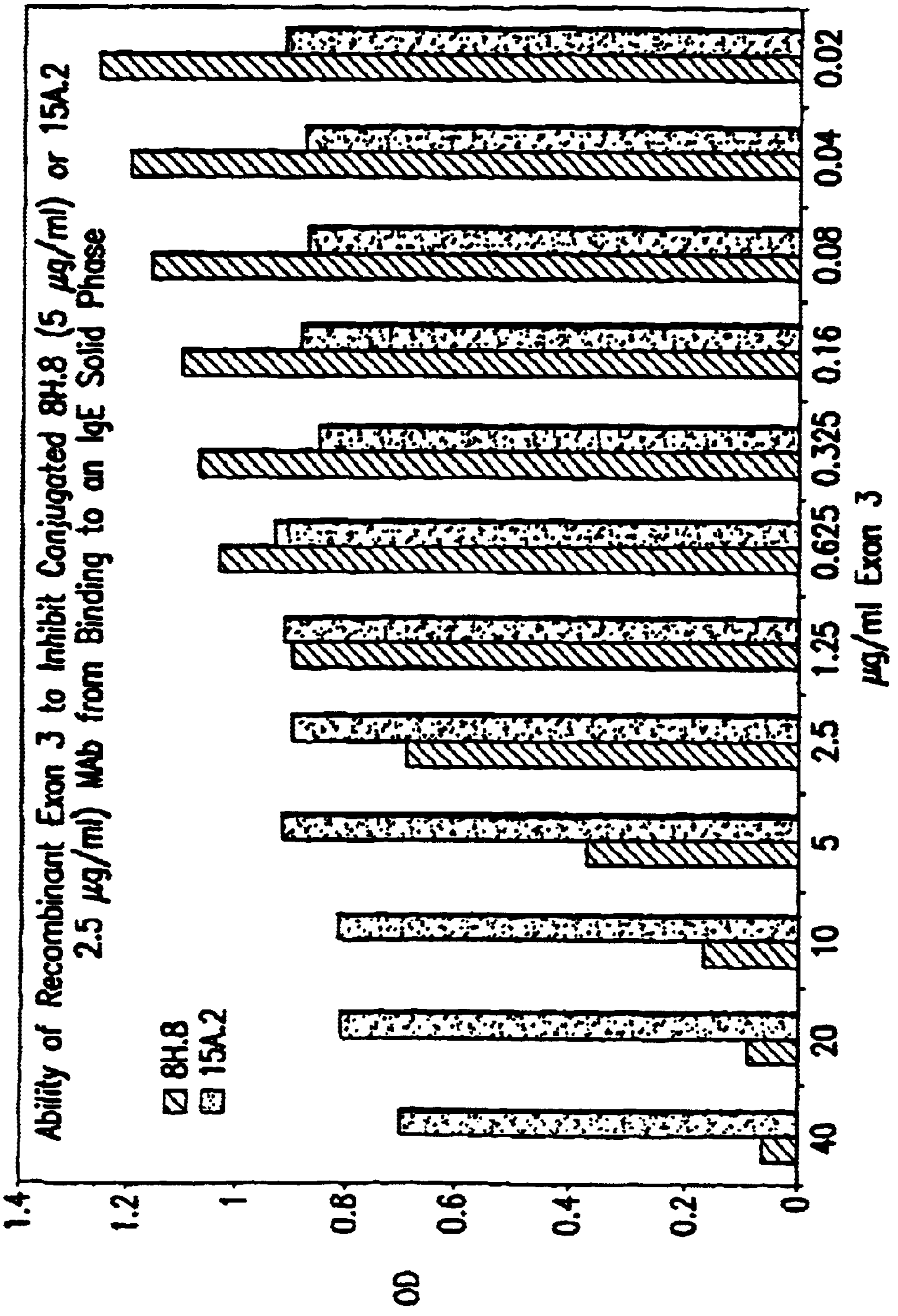
FIG. 3 depicts the ability of recombinant exon 3 to inhibit conjugated antibody 8H.8 or conjugated antibody 15A.2 from binding to an IgE solid phase. Data for 8H.8 is depicted by speckled bar graphs, data for 15A.2 is depicted by solid black bar graphs.

Competitive assays were performed between an antibody, 8H.8 or 15A.2, and soluble exon 3 to identify the level of inhibition of binding of these antibodies to affinity purified native IgE immobilized on the solid phase of an ELISA. The results from this study are depicted in FIG. 3. In FIG. 3 it is seen that increasing the concentration of recombinant exon 3 inhibited the binding of monoclonal antibody 8H.8, but did not inhibit antibody 15A.2.

In addition, the ability of these monoclonal antibodies to inhibit IgE from binding to recombinant IgE receptor on an ELISA solid phase was examined.

Figure 4:
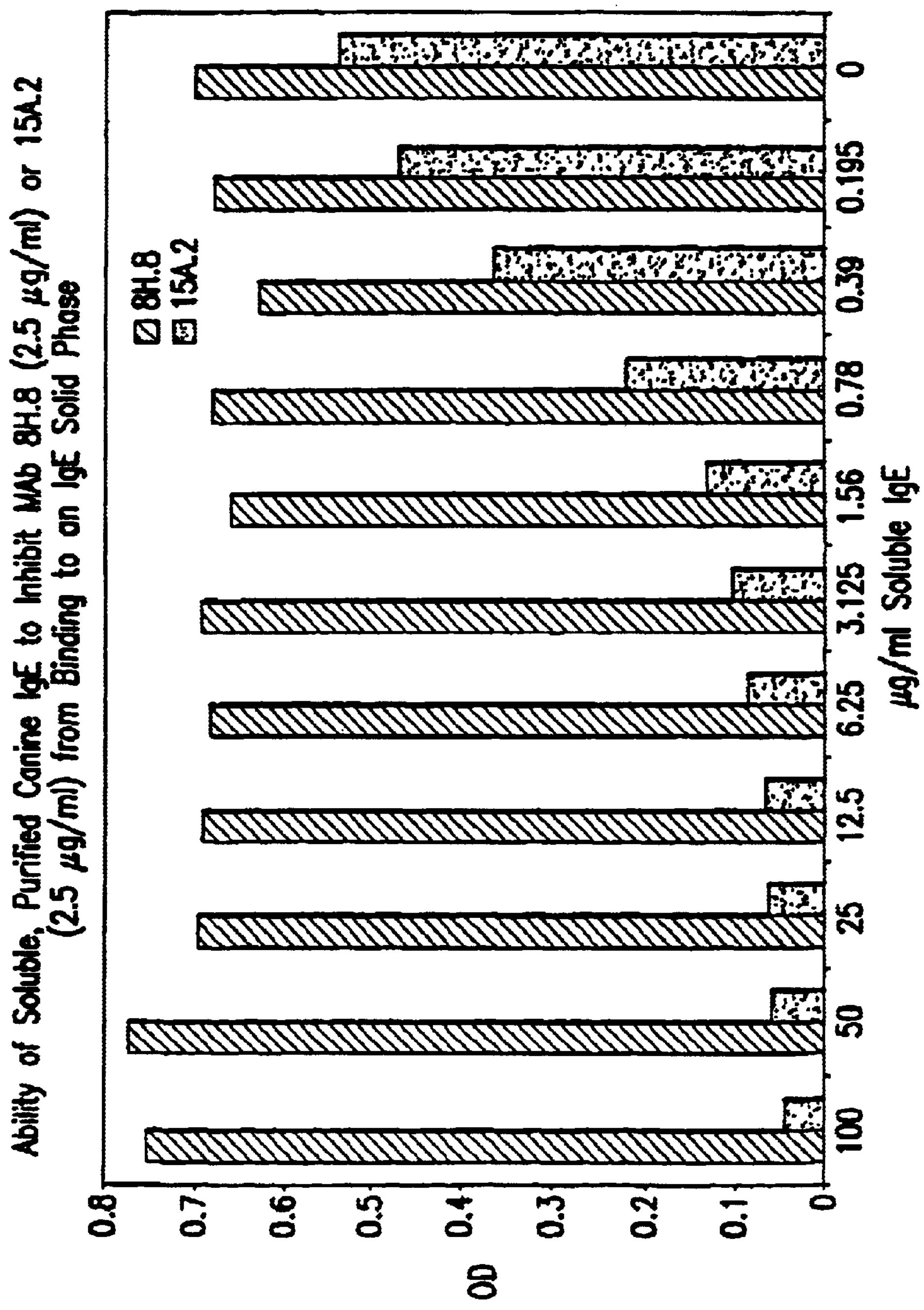
FIG. 4 depicts the ability of soluble, purified canine IgE to inhibit monoclonal antibody 8H.8 (2.5 μg/ml) or monoclonal antibody 15A.2 (2.5 μg/ml) from binding to a canine IgE solid phase. Data for 8H.8 is depicted by speckled bar graphs; data for 15A.2 is depicted by solid black bar graphs.

Additionally, competitive assays were performed with antibody 8H.8, and analogous assays were performed with 15A.2, where the antibody was in competition with affinity-purified canine IgE in solution and IgE on an ELISA solid phase. Data from these assays is depicted in FIG. 4.

These studies suggested that 15A.2 had a high affinity for soluble native canine IgE because as the concentration of the soluble IgE was increased, the binding of 15A.2 to the immobilized immunoglobulin dropped appreciably, indicating that 15A.2 was now binding to the soluble IgE. In contrast, it is seen that antibody 8H.8 has a much lower affinity for soluble IgE, because increasingly high concentrations of the soluble IgE did not inhibit the ability of 8H.8 to bind to the immobilized IgE. Thus, the data suggest that soluble IgE was not effective at inhibiting 8H.8 from binding to IgE immobilized on a solid phase. Thus, the affinity of 8H.8 for soluble canine IgE was lower than the affinity of this monoclonal antibody for IgE on a solid phase.

These studies further suggested that 8H.8 had a low affinity for soluble native canine IgE, because increasingly high concentrations of the soluble IgE did not inhibit the ability of 8H.8 to bind to the immobilized IgE. In contrast, it is seen that antibody 15A.2 has a much higher affinity for soluble IgE, since as the concentration of the soluble IgE was increased, the binding of 15A.2 to the immobilized immunoglobulin dropped appreciably, indicating that 15A.2 was now binding to the soluble IgE. Thus, the data suggested that soluble IgE was not effective at inhibiting 8H.8 from binding to IgE immobilized on a solid phase. Thus, the affinity of 8H.8 for soluble canine IgE was lower than the affinity of this monoclonal for IgE on a solid phase.

Figure 5:
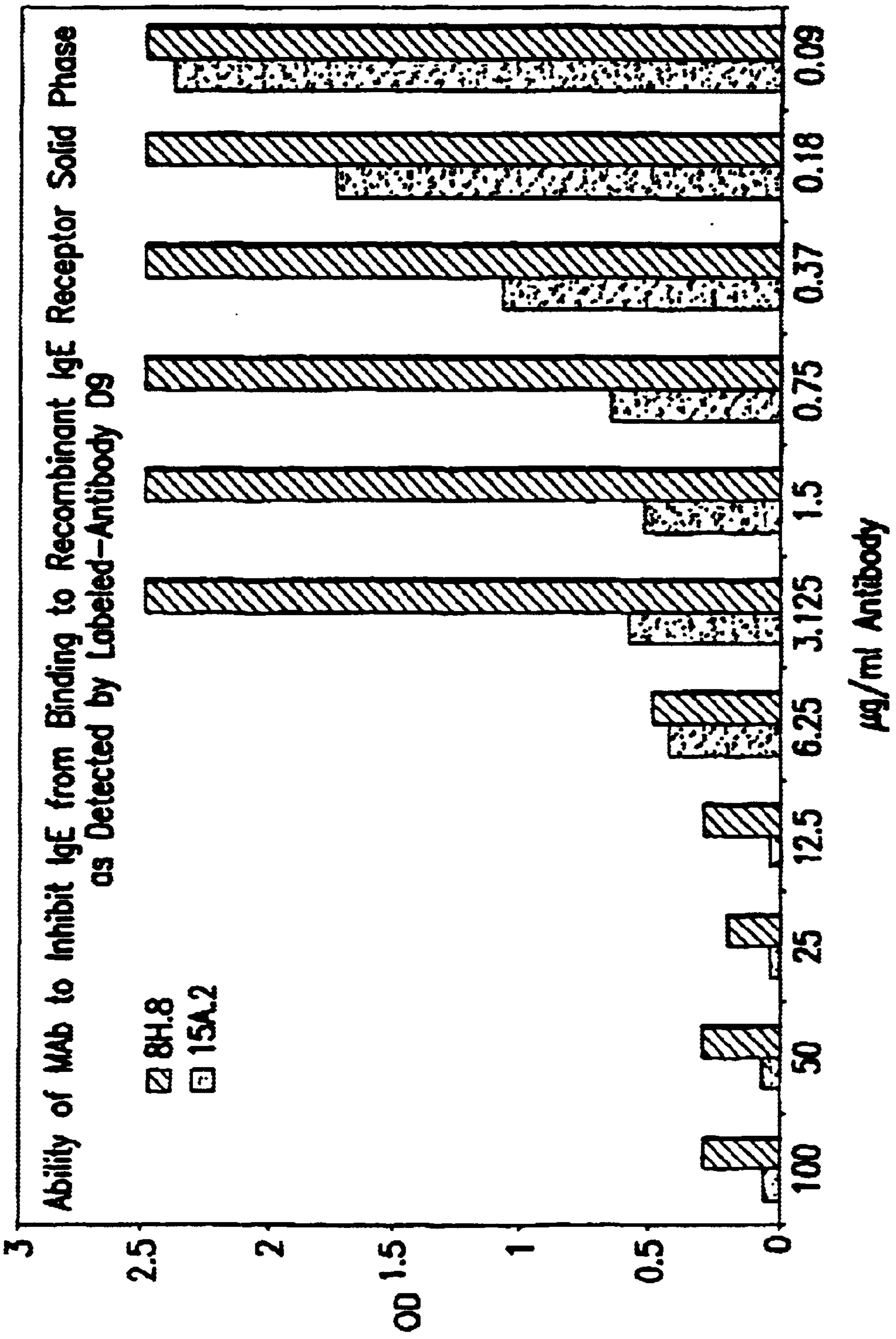
FIG. 5 depicts the ability of monoclonal antibody 15A.2 or monoclonal antibody 8H.8 to inhibit IgE from binding to recombinant IgE receptor immobilized on a solid phase as detected by monoclonal antibody D9.

To further substantiate the finding that 15A.2 has a higher affinity for soluble native IgE, and that 8H.8 had a low affinity for soluble native IgE, studies were performed where 8H.8 was used, and analogous studies were conducted with 15A.2, to determine the extent to which each antibody inhibits binding of the soluble IgE to a recombinant IgE receptor solid phase. A labeled antibody D9 was used as a means for detection in the studies depicted in FIG. 5. The monoclonal antibody D9 is known to bind to IgE when bound to receptor. For the studies depicted in FIG. 5, the native IgE was present at a concentration of 2.5 micrograms per milliliter. As shown in FIG. 5, 15A.2 was effective at inhibiting binding of the native IgE to recombinant IgE receptor at antibody concentrations as low as 190 nanograms per milliliter. In contrast, 3,125 nanograms per milliliter of 8H.8 were necessary to inhibit the binding of native IgE to the recombinant IgE receptor. Thus, since more 8H.8 than 15A.2 was required to inhibit the binding of native IgE to the recombinant receptor, it was seen that 8H.8 had a lower affinity for the soluble IgE. It appears, therefore, that when a sufficient concentration of either 8H.8 or 15A.2 antibodies is provided, that the antibodies impair the binding of soluble IgE to the IgE receptor.

Furthermore, as indicated by the data depicted in FIG. 2, the avidity of 8H.8 binding for native canine IgE was greatly increased when the IgE was immobilized. These studies suggested that 8H.8 had a low affinity for soluble native canine IgE, but that when the IgE is immobilized on a surface, or when it is expressed on the surface of a memory B cell, the avidity of 8H.8 binding for native canine IgE was greatly increased.

Accordingly, in view of these findings, it was hypothesized that the region within native IgE recognized by 8H.8 might be partially hidden, particularly when the IgE is in serum. A partially sequestered amino acid sequence of IgE may not be readily exposed to the native canine immune system and its normal protective mechanisms. Furthermore, since the full length exon 3 did not lead to the generation of antibodies having 8H.8-like specificity, the full length sequence might contain suppressor peptides capable of down-regulating or eliminating an auto-anti-IgE response which is specific against the epitope recognized by the 8H.8 antibody. Either mechanism could serve to avoid production of an autoimmune response to self-antigens.

The implications of these findings are that 8H.8 antibody, when used as an allergy therapeutic in dogs, would preferentially bind to IgE on memory B cells rather than to IgE in solution. Moreover, 8H.8 has a low binding affinity for IgE when bound by Fc receptor on mast cells.

Phage display technology was used to map the epitope bound by the 8H.8 antibody. A preferred method for performing phage display technology is accomplished by use of a Ph.D. Phage Display Peptide Library Kit (New England BioLabs, Beverly Mass.). It was found that a 7 amino acid peptide (Thr-Leu-Leu-Glu-Tyr-Arg-Meth) (SEQ ID NO:4) inhibited monoclonal antibody 8H.8 from competitive binding to either native or recombinant canine IgE. This sequence contained 6 amino acids common in form and/or spacing to the C-terminal region of exon 3. An 11 amino acid peptide synthesized from this region Gly-Met-Asn-Leu-Thr-Trp-Tyr-Arg-Glu-Ser-Lys (SEQ ID NO:5) designated E3a.5 also inhibited monoclonal antibody 8H.8 from competitive binding to native or recombinant IgE.

It is believed that antibody responses with specificity such as that of 8H.8 do not occur naturally, even upon occurrence of events which would induce auto-anti-IgE responses to other epitopes, because the 8H.8 epitope is only partially available for recognition. Nevertheless, it is hypothesized that antibodies to an 8H.8-type epitope, generated from peptide immunization in accordance with the invention do bind to the partially available epitope, as does the 8H.8 monoclonal antibody.

It is further hypothesized that the region within native IgE recognized by 15A.2 might serve as an immunogen to induce auto-anti-IgE responses and might generate antibodies capable of binding to IgE+ B cells and of down regulating IgE synthesis. The implications of these findings are that 15A.2 antibody, when used as an allergy therapeutic in dogs, would prevent IgE from binding to mast cells and potentially affect the synthesis of IgE by B cells.

Phage display technology was used to map the epitope bound by the 15A.2 antibody. As noted above, a preferred method for performing phage display technology is accomplished by use of a Ph.D. Phage Display Peptide Library Kit (New England BioLabs, Beverly Mass.). FIG. 6 depicts the amino acid sequences of the PhDc7c library that were bound by the monoclonal antibody 15A.2. These sequences are shown in alignment with the protein sequence of canine IgE. FIG. 7 depicts the alignment of the 15A.2 epitope from seven different mammals: dog, human, green monkey, cat, swine, mouse and horse.

Figure 8:
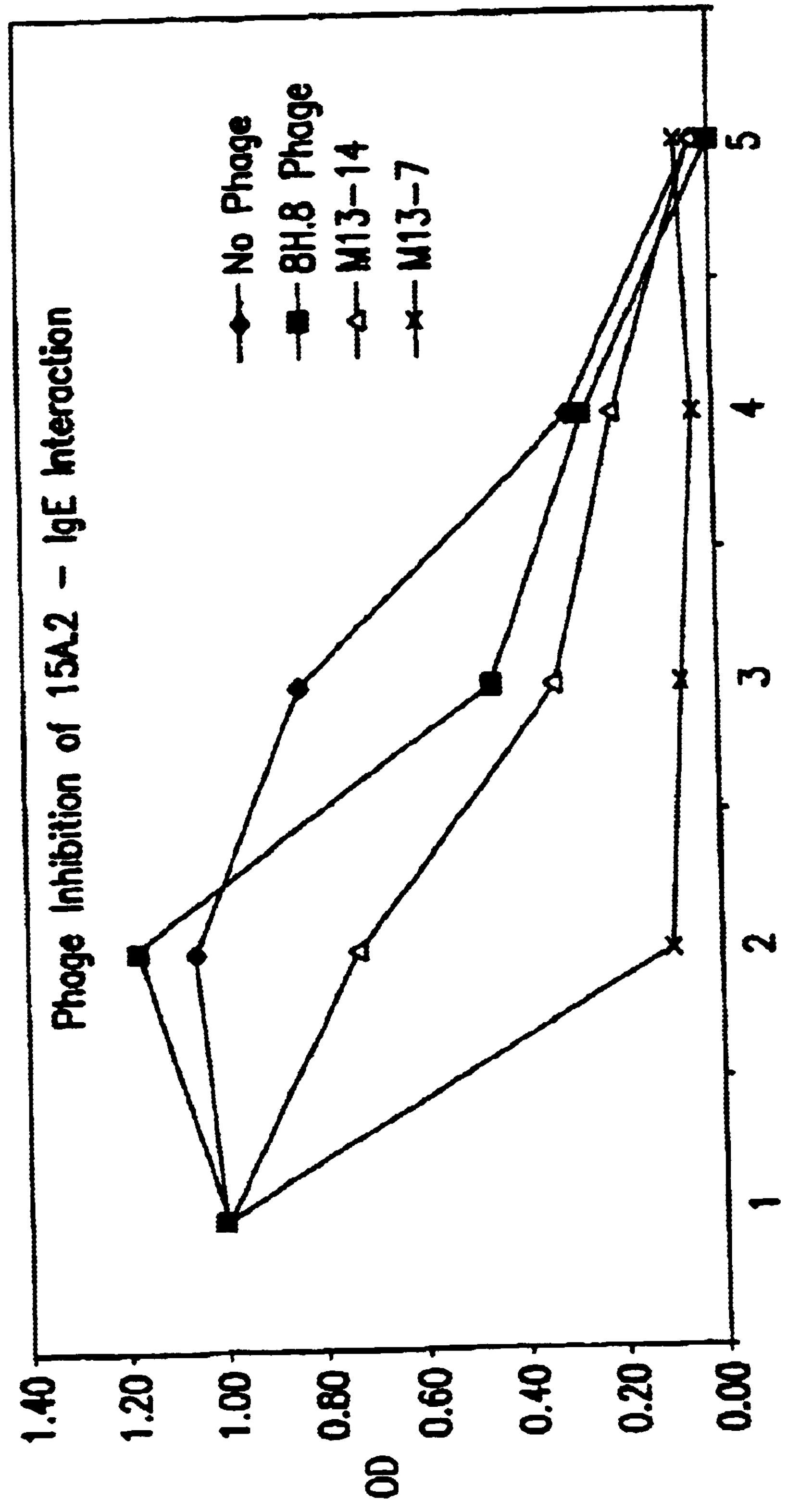
FIG. 8 depicts the ability of phage displaying 15A.2 mimotope peptides to inhibit canine IgE from binding the 15A.2 monoclonal antibody on the solid phase.

FIG. 8 portrays the ability of different phage displaying 15A.2 mimotope peptides to inhibit canine IgE from binding the 15A.2 monoclonal antibody on the solid phase. 466 μl of biotinylated 15A.2 antibody (10 μg/ml) were mixed with 466 μl of phage from a fresh overnight culture. Into each well of a microtiter plate 100 μl of the mixture was added. The antibodies and phage were allowed to bind for 2½ hours. The wells were then coated with strepavidin. The plates were washed three times with standard wash buffer to remove loosely bound material. A serial dilution of canine IgE was prepared, starting with the concentration of 1 μg/100 μl of PBS, 0.1% Tween. 100 μl of dilution IgE was added per well and allowed to bind for 10 minutes. The competition reaction was stopped by washing the plates five times with wash solution. The plate was then developed with HRPO linked D9 monoclonal antibody, which binds to domain 4 of IgE, to visualize the IgE in the solid phase. Loss of signal indicates the phage successfully repelled canine IgE competition. Table 1 shows the concentrations of the reactants at the various points on the x-axis of FIG. 8.

TABLE 1

| | IgE | phage |
|---|---|---|
| 1 | 1.0 μg | 0 |
| 2 | 1.0 μg | 50 μl |
| 3 | 0.5 μg | 50 μl |
| 4 | 0.25 μg | 50 μl |
| 5 | 0.125 μg | 50 μl |

Using the New England Biolabs PhD12 phage display library, it was found that a 12 amino acid peptide (SEQ ID NO:11 Val-Thr-Leu-Cys-Pro-Asn-Pro-His-Ile-Pro-Met-Cys) inhibited monoclonal antibody 15A.2 from competitive binding to either native or recombinant canine IgE. This sequence contained 4 amino acids common in form and/or spacing to the N-terminal region of exon 3.

Figure 9:
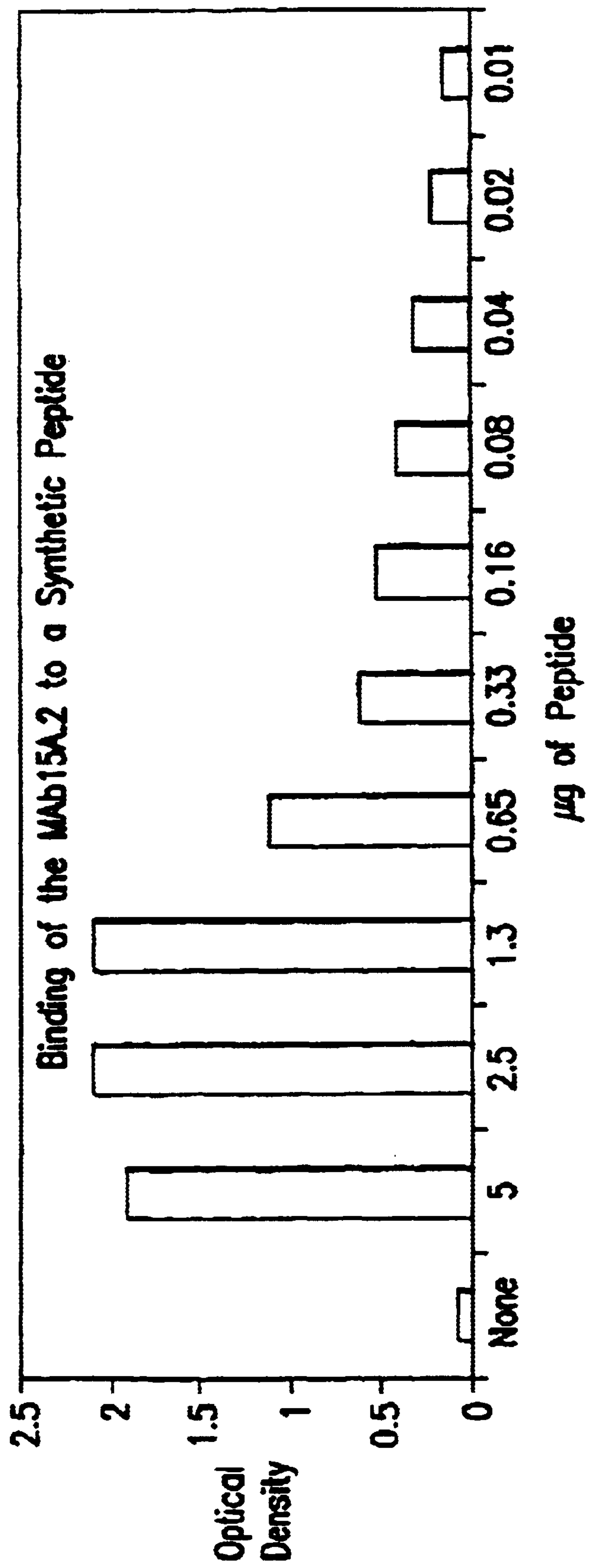
FIG. 9 depicts the ability of a specific 15A.2 mimotope peptide sequence attached to the solid phase to be able to bind the 15A.2 mimotope monoclonal antibody.

FIG. 9 displays the ability of 15A.2 monoclonal antibody to bind a synthetic peptide. The peptide SEQ ID NO:12 Ser-Val-Thr-Leu-Cys-Pro-Asn-Pro-His-Ile-Pro-Met-Cys-Gly-Gly-Gly-Lys was synthesized and biotinylated on the epsilon carbon of the Lys residue. This sequence corresponds to the isolate M13-48. The peptide was treated in a manner to promote reduction and cyclization of the cysteines to form a cyclic peptide. A serial dilution of the peptide was prepared and bound to strepavidin-coated microtiter plates (5 μg strepavidin per well). Bound peptide was detected with HRPO conjugated 15A.2 monoclonal antibody. FIG. 9 shows the results of this experiment. This solid phase specific 15A.2 mimotope peptide bound the 15A.2 monoclonal antibody in a concentration dependent manner.

Figure 10A:
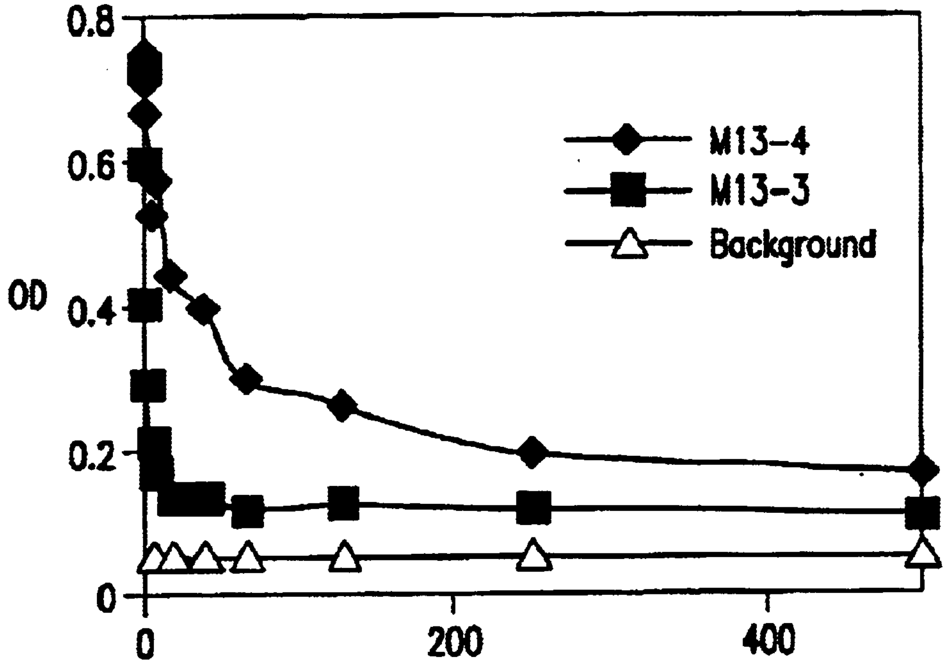
FIGS. 10A and 10B depict the ability of a 15A.2 mimotope, peptide to be able to prevent the 15A.2 monoclonal antibody from binding canine IgE on the solid phase.
Figure 10B:
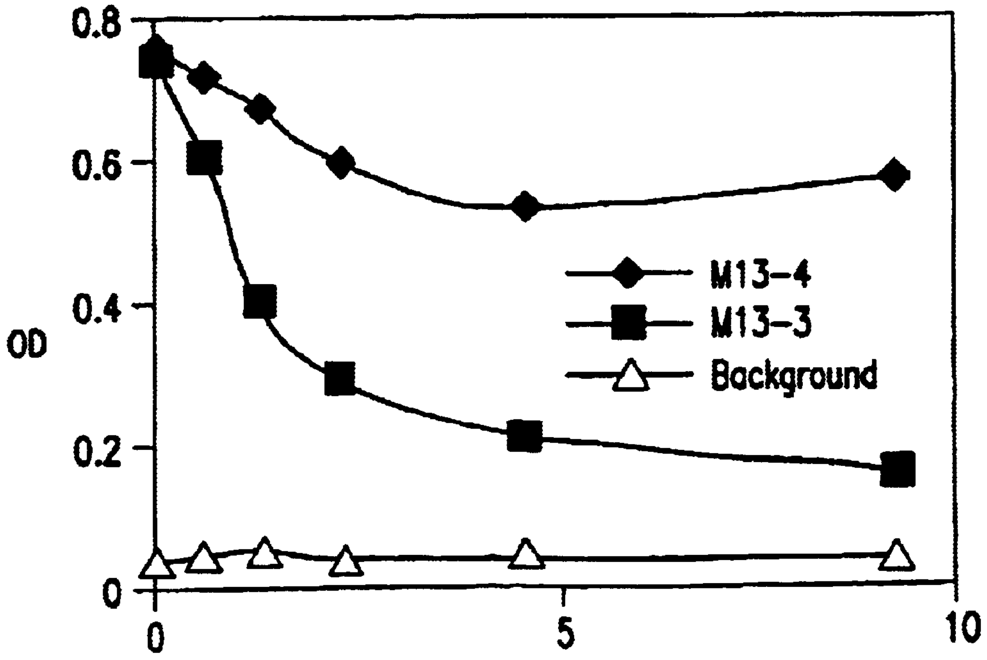

FIGS. 10A and 10B depict the ability of a 15A.2 mimotope peptide to prevent the 15A.2 monoclonal antibody from binding canine IgE on the solid phase. Plates were coated with canine IgE at a concentration of 1 μg/ml. A serial dilution of the synthetic peptide was added to HRPO conjugated 15A.2 monoclonal antibody (final concentration 1 μg/ml) and allowed to bind for two hours. 100 μl of the 15A.2/peptide mixture was added to the wells and allowed to bind 1 hour. The reaction was stopped by washing the plates six times with wash buffer. The plates were developed with HRPO substrate, the reactions stopped with stop mix, and the plates were measured for O.D. using a plate reader.

Apart from active immunization with antibody 15A.2 or 8H.8 to induce auto-anti-IgE production in vivo, this invention also comprises a specific binding molecule that specifically binds a ligand of the type bound by 15A.2 or 8H.8, as well as the therapeutic or prophylactic use thereof. Thus, the invention comprises a monoclonal antibody specific for a conservative variant of a sequence bound by 15A.2, for a conservative variant of a sequence bound by 8H.8, or for a native sequence of canine IgE up to 100 amino acids from the C' terminal portion of exon 3. The specific binding molecules of the invention can be used in a method in accordance with the invention as a treatment for or as prophylaxis for allergy symptoms, i.e., passive immunization.

Accordingly, administration to a dog of either an antibody in accordance with the invention, such as 15A.2 or 8H.8, or a peptide in accordance with the invention, such as the 7, 11 or 12 amino acid peptide, leads to a diminution of further IgE production. This may occur, for example, by the 15A.2 or 8H.8 antibody binding to the memory B cell and preventing further IgE production. For a peptide, its administration would lead to production of antibodies of comparable specificity and effect as 15A.2 or 8H.8.

EXAMPLES

Example 1

Figure 11:
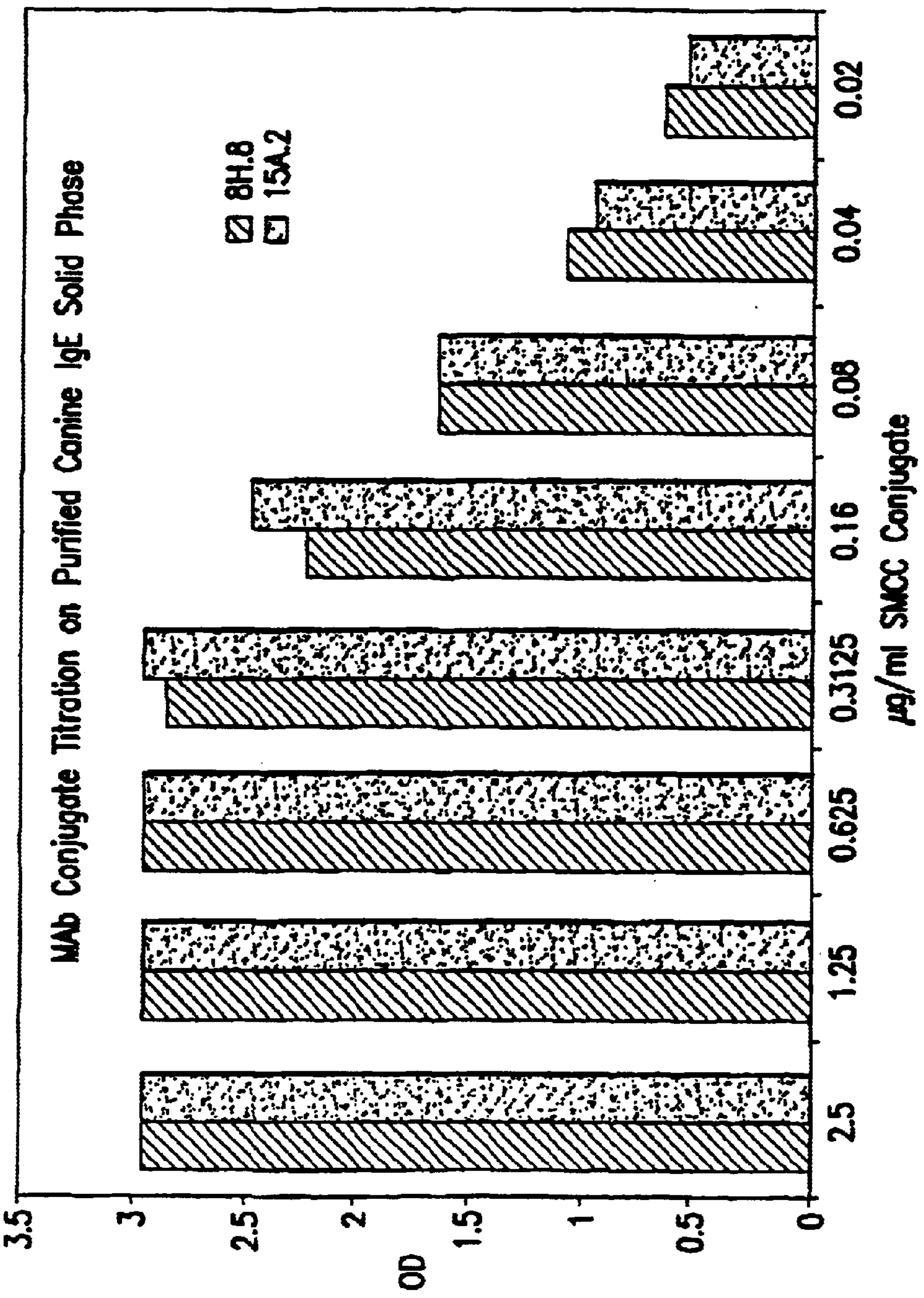
FIG. 11 depicts the ability of monoclonal antibody 8H.8 and monoclonal antibody 15A.2 to bind to purified canine IgE immobilized on a solid phase.

FIG. 11 depicts results of the binding study where antibody 8H.8 and antibody 15A.2 were separately assayed to determine their ability to bind to a solid phase having affinity purified canine IgE immobilized thereon. These results showed that those 8H.8 and 15A.2 bind to native IgE when immobilized on a solid phase. The results from these studies suggest that the binding of each of these antibodies to the surface bound IgE was of comparable affinity. To determine whether the affinity of binding of each antibody was, in fact, comparable, further studies were performed.

Figure 12:
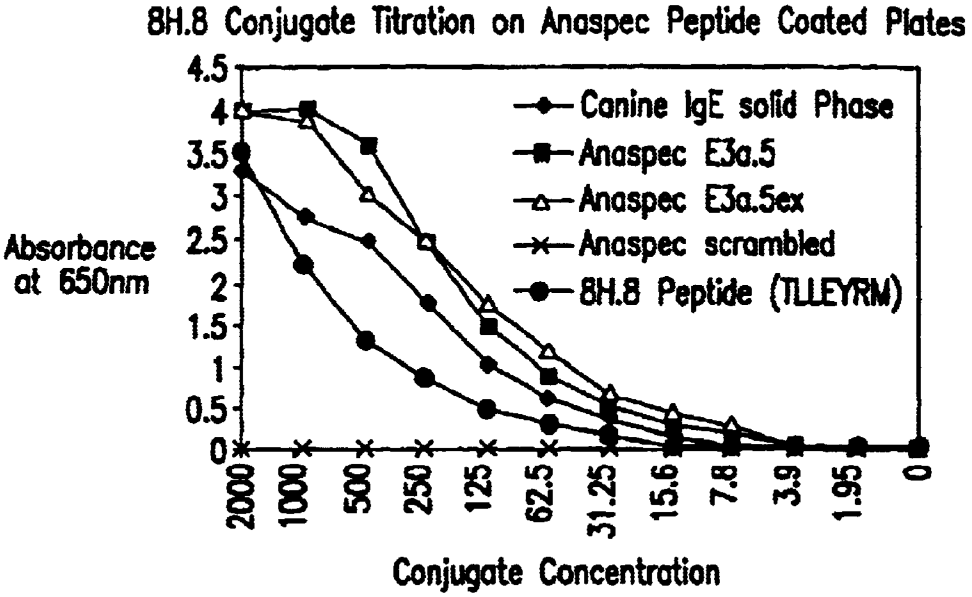
FIG. 12 depicts data from a study evaluating the ability of antibody 15A.2 conjugated to a signal moiety to bind to solid phases having various peptides immobilized thereon.

FIG. 12 depicts results of the study where antibody 8H.8 conjugated to a signal moiety was reacted at various concentration with solid phases having various peptides immobilized thereon. The data depicted by (★) reflects a solid phase having canine IgE immobilized thereon; data depicted by (■) depicts solid phase having E3a.5 immobilized thereon; data depicted by (π) depicts solid phase have E3a.5 extended peptide immobilized thereon, data depicted by an (X) reflects data for a solid phase having an E3a.5 scrambled peptide immobilized thereon, data depicted by (★) depicts data for solid phase having the seven amino acid peptide identified by phage display technology to which 5H8 binds immobilized thereon. Thus, it is seen that 8H.8 binds to each solid phase with the exception solid phase having the E3a.5 scrambled peptide.

Figure 13:
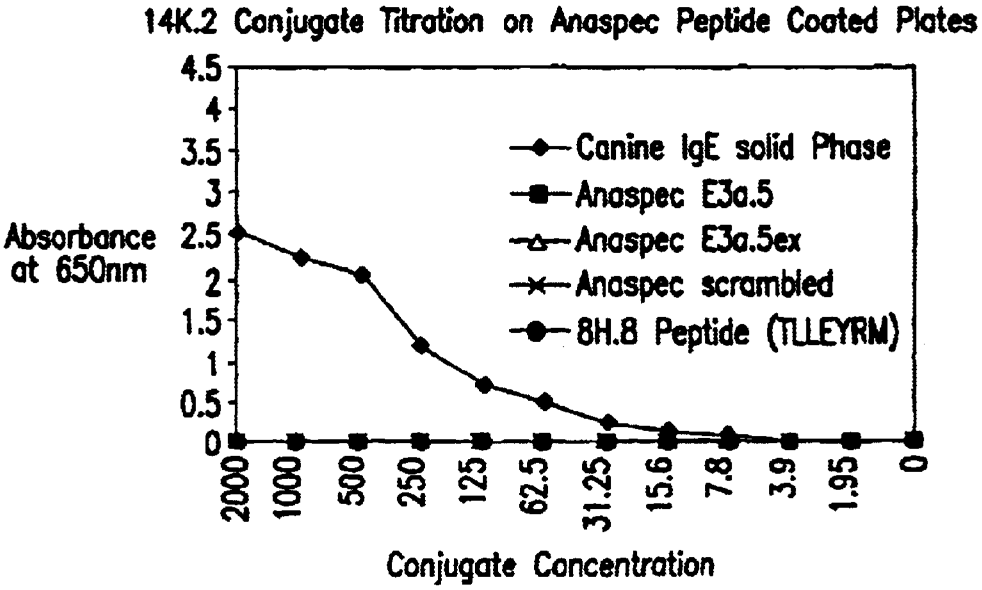
FIG. 13 depicts data from a study evaluating the ability of monoclonal antibody 14K2, known to bind with canine IgE exon 4, to bind with various peptides immobilized on a solid phase.

Monoclonal antibody 14K2 is known to bind exclusive to canine IgE exon 4. This monoclonal antibody was reacted with various solid phases having different peptides immobilized thereon. The data depicted by (♦) reflects a solid phase having canine IgE immobilized thereon; data depicted by (U) depicts solid phase having E3a.5 immobilized thereon; data depicted by (π) depicts solid phase have E3a.5 extended peptide immobilized thereon; data depicted by an (X) reflects data for a solid phase having an E3a.5 scrambled peptide immobilized thereon; and data depicted by (★) depicts data for solid phase having the seven amino acid peptide identified by phage display technology to which 8H.8 binds immobilized thereon. Thus, it is seen that 14K2 only binds to a solid phase having the entire canine IgE molecule immobilized thereon. This data is depicted in FIG. 13.

Figure 14:
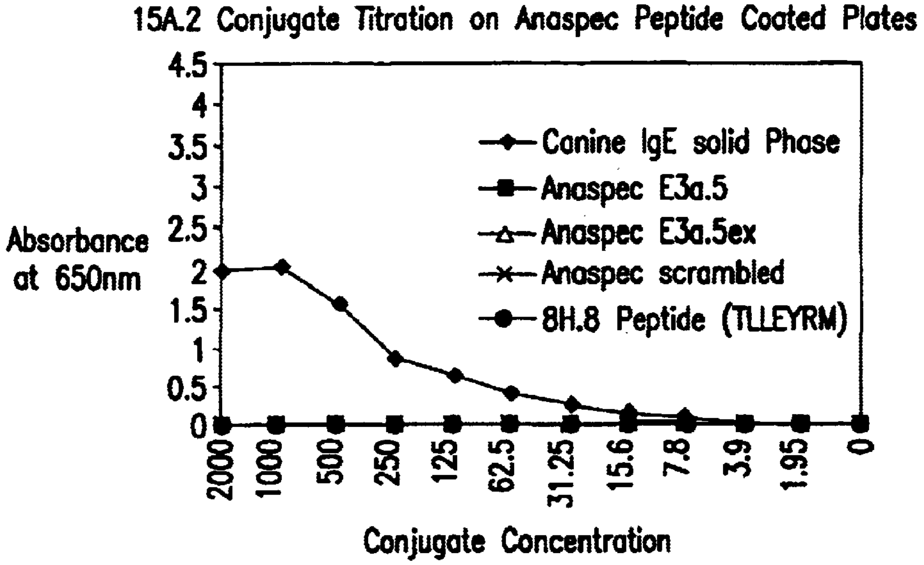
FIG. 14 depicts data from a study evaluating the ability of monoclonal antibody 15A.2, known to bind to canine IgE exon 3, to bind to various peptides immobilized on a solid phase.

Monoclonal antibody 15A.2 is believed to bind only to canine IgE exon 3. FIG. 14 depicts data for studies which evaluated the binding of 15A.2 to various peptides. The data depicted by (♦) reflects a solid phase having canine IgE immobilized thereon; data depicted by (■) depicts solid phase having E3a.5 immobilized thereon; data depicted by (π) depicts solid phase have E3a.5 extended peptide immobilized thereon, data depicted by an (X) reflects data for a solid phase having an E3a.5 scrambled peptide immobilized thereon, data depicted by (★) depicts data for solid phase having the seven amino acid peptide identified by phage display technology to which 8H.8 binds immobilized thereon. These binding studies showed that 15A.2 bound only to a solid phase which had the entire canine IgE molecule immobilized thereon. This data indicated that 15A.2 does not bind the same epitope as that bound by 8H.8.

Figure 15:
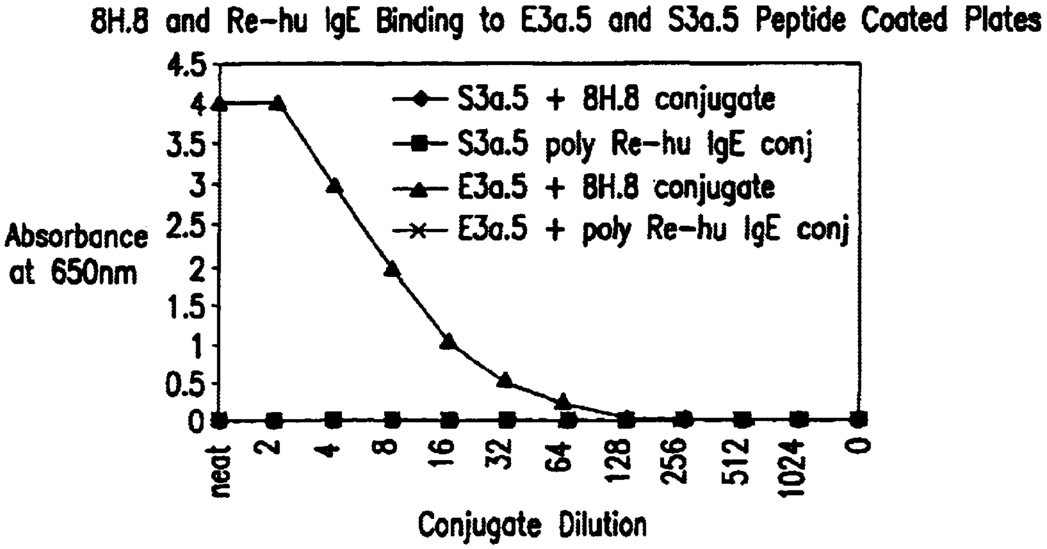
FIG. 15 depicts data for studies that compared the binding of monoclonal antibody 8H.8, or a polyclonal antibody raised to recombinant IgE (Re-hu IgE), to bind to a solid phase having peptide E3a.5 or substituted peptide E3a.5 (designated peptide S3a.5) immobilized thereon.

FIG. 15 depicts data for studies that compare the binding of 8H.8 or polyclonal antibodies raised to recombinant human IgE, to peptide E3a.5 or to peptide E3a.5 with an amino acid substitution making the peptide more analogous to a sequence in the human genome which encodes human IgE, designated peptide S3a.5. In FIG. 15 data depicted by the (♦) reflects substituted 3a.5 compared with 8H.8; data depicted by (♦) reflects substituted peptide 3a.5 and Re-Hu IgE: data depicted by (π) reflects peptide E3a.5 and 8H.8 and, data depicted by and (X) reflects data regarding peptide E3a.5 and polyclonal Re Hu IgE. These data indicated that only 8H.8 became bound to E3a.5 on a solid phase, no other combination exhibited binding.

Figure 16:
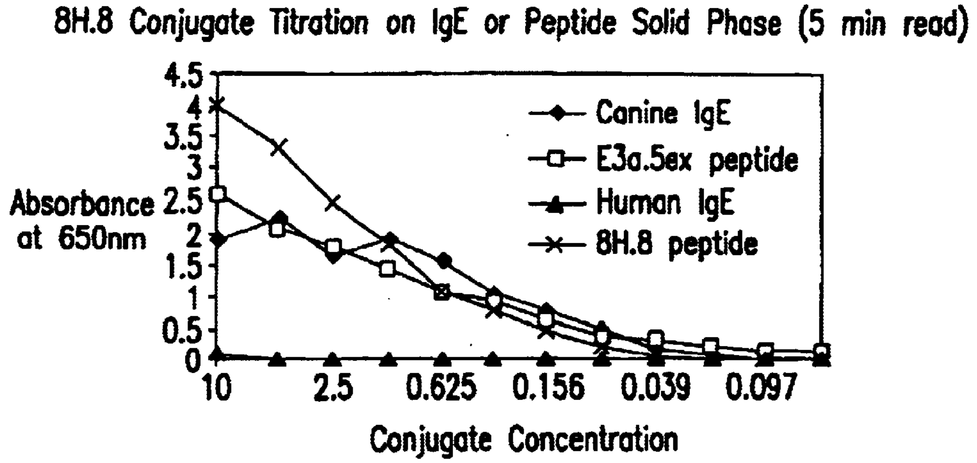
FIG. 16 depicts data from a study evaluating the ability of antibody 8H.8 conjugated to a signal moiety to bind to solid phases having various peptides immobilized thereon.

FIG. 16 depicts the data on studies that compared the binding of 8H.8 to various peptides immobilized on a solid phase. Data depicted by (♦) reflects data for a solid phase having canine IgE immobilized thereon; data depicted by (♦) reflects data for a solid phase having a peptide E3a.5 extended immobilized thereon; data depicted by (π) reflects data for a solid phase having human IgE immobilized thereon and, data depicted by an (X) reflects data for a solid phase having a 8H.8 peptide immobilized thereon. Accordingly it is seen that 8H.8 binds to canine IgE, peptide E3a.5 extended or the seven amino acid peptide identified by phage display technology as the binding epitope for 8H.8, when each of these peptides were immobilized on a solid phase. Additionally, it is seen that 8H.8 does not bind to human IgE.

Figure 17:
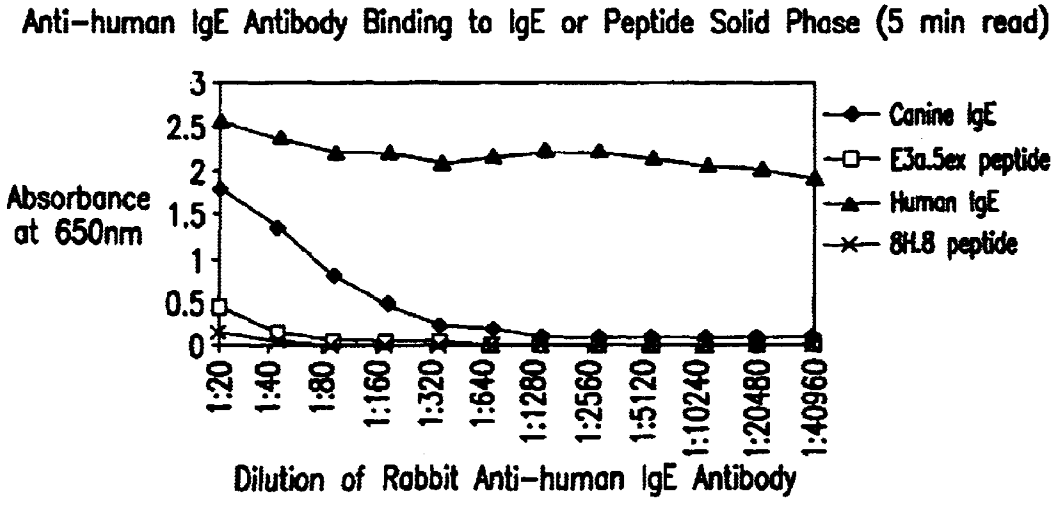
FIG. 17 depicts the ability of polyclonal anti-human IgE antibodies to bind to various peptides immobilized on a solid phase.

FIG. 17 depicts data for studies which compare the ability of polyclonal anti human IgE antibodies ability to bind to solid phases having various peptides immobilized thereon. Data depicted by (★) reflects data for a solid phase having canine IgE immobilized thereon; data depicted by (■) reflects data for a solid phaae having a peptide E3a.5 extended immobilized thereon; data depicted by (π) reflects data for a solid phase having human IgE immobilized thereon and, data depicted by an (X) reflects data for a solid phase having a 8H.8 peptide immobilized thereon. Thus, it was seen that the anti-human IgE polyclonal antibodies bound to human IgE when immobilized on a solid phase. It was also seen that the polyclonal antiserum exhibited limited binding to peptide E3a.5 extended when the polyclonal antibodies were present at very high concentrations; this was believed to be a binding artifact due to the high antibody concentration. Thus, it was found that antibodies to Human IgE do not specifically bind to canine IgE or to peptides in accordance with the invention.

Example 2

The amino acid sequences for the epitope bound by 8H.8, the 11 amino acid sequence used in the immunization studies presented herein, as well as analogous sequences from feline and Human IgE sequences are set forth in Table 2. Additionally, a substituted canine sequence was prepared having an amino acid substitution which made the peptide more closely analogous to the human peptide.

TABLE 2

| Species/Source | Sequence | SEQ ID NO. |
|---|---|---|
| mimotope bound by 8H.8 | T—L—L—E—Y—R—N | 4 |
| canine | G—M—N—L—T—W—Y—R—E—S—K | 5 |
| human | V—N—L—T—W—S—R | 13 |
| feline | G—M—T—L—T—W—S—R—E—N—G | 14 |
| Substituted Canine Sequence | G—M—N—L—T—W—S—R—E—S—K | 15 |

Each of the peptides in Table 2 was placed on a solid phase and studies were performed to identify if 8H.8 would bind to the surface-bound peptide. It was found that 8H.8 bound to a surface having the mimotope peptide thereon, and to a surface having the 11 amino acid peptide bound thereon. It was found that 8H.8 did not bind to the human peptide, the feline peptide or to the canine sequence which had an amino acid substitution which made it more analogous to the human sequence, when either of these peptides were surface bound.

Closing

As used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to or equivalent to those described herein can be used in the practice or testing of the invention, the preferred methods and materials are now described. All publications mentioned herein are fully incorporated herein by-reference.

What is claimed is:

1. A specific binding protein selected from the group consisting of a monoclonal antibody, a polyclonal antibody, an antigen-binding fragment of a monoclonal antibody, antigen-binding fragment of a polyclonal antibody, a hybrid antibody, and a single chain antibody, which specifically binds to an isolated and purified peptide comprising an amino acid sequence which consists essentially of Thr-Leu-Leu-Glu-Tyr-Arg-Met (SEQ ID NO:4), or a conservative variant thereof, wherein the conservative variant comprises an amino acid substitution at amino acid position 3, 4 or both 3 and 4.

2. The specific binding protein of claim 1 wherein at least one amino acid substitution is an amino acid with an aromatic ring.

3. A specific binding protein selected from the group consisting of a monoclonal antibody, a polyclonal antibody, an antigen-binding fragment of a monoclonal antibody, antigen-binding fragment of a polyclonal antibody, a hybrid antibody, and a single chain antibody, which specifically binds to an isolated and purified peptide comprising an amino acid sequence which consists essentially of Gly-Met-Asn-Leu-Thr-Trp-Tyr-Arg-Glu-Ser-Lys (SEQ ID NO:5), or a conservative variant thereof, wherein the conservative variant comprises an amino acid substitution at amino acid position 5, 6 or both 5 and 6.

4. A specific binding protein selected from the group consisting of a monoclonal antibody, a polyclonal antibody, an antigen-binding fragment of a monoclonal antibody, antigen-binding fragment of a polyclonal antibody, a hybrid antibody, and a single chain antibody, which specifically binds to an isolated and purified peptide consisting essentially of SEQ ID NO:4.

5. A specific binding protein selected from the group consisting of a monoclonal antibody, a polyclonal antibody, an antigen-binding fragment of a monoclonal antibody, antigen-binding fragment of a polyclonal antibody, a hybrid antibody, and a single chain antibody, which is raised to a multiply antigen peptide comprising multiple copies of an isolated and purified peptide which consists essentially of SEQ ID NO:4, SEQ ID NO:5, or both SEQ ID NO:4 and SEQ ID NO:5.

6. A specific binding protein selected from the group consisting of a monoclonal antibody, a polyclonal antibody, an antigen-binding fragment of a monoclonal antibody, antigen-binding fragment of a polyclonal antibody, a hybrid antibody, and a single chain antibody, which is raised to a recombinant plant virus particle comprising at least one copy of an isolated and purified peptide comprising SEQ ID NO:4, SEQ ID NO:5 or both SEQ ID NO:4 and SEQ ID NO:5.

7. A monoclonal antibody produced by hybridoma 8H.8 having ATCC accession number PTA-4597.

8. A specific binding protein selected from the group consisting of a monoclonal antibody, a polyclonal antibody, an antigen-binding fragment of a monoclonal antibody, antigen-binding fragment of a polyclonal antibody, a hybrid antibody, and a single chain antibody, which specifically binds to an opitope bound by the antibody of claim 7.

* * * * *